United States Patent
Cho et al.

(10) Patent No.: US 10,799,719 B2
(45) Date of Patent: Oct. 13, 2020

(54) MONITORING SYSTEM FOR THERMOPLASTIC MASK USING PRESSURE SENSOR

(71) Applicant: The Catholic University of Korea Industry-Academic Cooperation Foundation, Seoul (KR)

(72) Inventors: Min-Seok Cho, Gyeonggi-do (KR); Tae-Ho Kim, Gyeonggi-do (KR); Seong-Hee Kang, Gyeonggi-do (KR); Dong-Su Kim, Gyeonggi-do (KR); Kyeong-Hyeon Kim, Gyeonggi-do (KR); Dong-Seok Shin, Incheon (KR); Si Yong Kim, Glen Allen, VA (US); Tae Suk Suh, Seoul (KR)

(73) Assignee: The Catholic University of Korea Industry-Academic Cooperation Foundation, Seoul (KR)

( * ) Notice: Subject to any disclaimer, the term of this patent is extended or adjusted under 35 U.S.C. 154(b) by 130 days.

(21) Appl. No.: 15/565,591

(22) PCT Filed: Mar. 31, 2016

(86) PCT No.: PCT/KR2016/003296
§ 371 (c)(1),
(2) Date: Oct. 10, 2017

(87) PCT Pub. No.: WO2016/159669
PCT Pub. Date: Oct. 6, 2016

(65) Prior Publication Data
US 2018/0256921 A1   Sep. 13, 2018

(30) Foreign Application Priority Data

Apr. 1, 2015 (KR) .................. 10-2015-0045939

(51) Int. Cl.
*A61N 5/10* (2006.01)
*G01L 1/04* (2006.01)
*G01L 7/18* (2006.01)

(52) U.S. Cl.
CPC ......... *A61N 5/1049* (2013.01); *A61N 5/1064* (2013.01); *A61N 5/1067* (2013.01); *A61N 2005/1097* (2013.01); *G01L 1/04* (2013.01); *G01L 7/182* (2013.01)

(58) Field of Classification Search
CPC ... A61N 5/1049; A61N 5/1064; A61N 5/1048
USPC ........................................................ 600/1-8
See application file for complete search history.

(56) References Cited

FOREIGN PATENT DOCUMENTS

WO   WO-2009067428 A1 *   5/2009   ............... A61B 6/04

* cited by examiner

Primary Examiner — John P Lacyk
(74) Attorney, Agent, or Firm — Huffman Law Group, PC

(57) ABSTRACT

The present invention relates to a thermoplastic mask monitoring system using a pressure sensor. Specifically, a thermoplastic mask according to the present invention may include: a mask having a shape determined according to a shape of a first region which is at least a part of a patient's body by using thermoplasticity, fixing the first region in close contact with the first region, and receiving radiation; and a pressure sensor provided between the mask and the first region and sensing pressure induced by a space generated between the mask and the first region.

15 Claims, 14 Drawing Sheets

FIG.13C
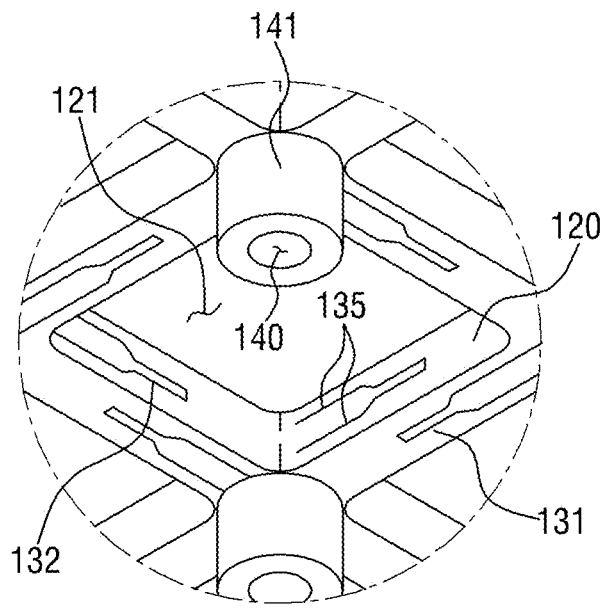
FIG.13C
FIG.14A
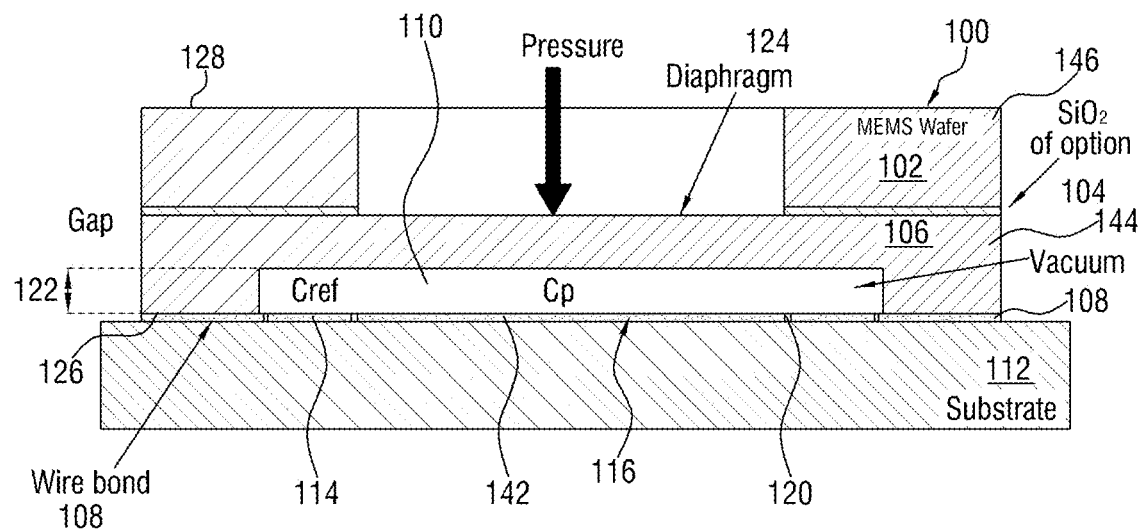

MONITORING SYSTEM FOR THERMOPLASTIC MASK USING PRESSURE SENSOR

TECHNICAL FIELD

The present invention relates to a thermoplastic mask monitoring system using a pressure sensor. Particularly, the present invention relates to a system for supporting safe radiation therapy of a patient by determining movement of a head within a mask through a pressure sensor provided between a mask and a body in a therapy of head and neck cancer using radiation.

BACKGROUND ART

A radiation source used in a radiation therapy apparatus generates radiation and is mounted on a gantry disposed around a therapy zone.

However, in head and neck radiotherapy, since a therapy target itself is a very sensitive part of a body, a very precise radiotherapy device is required and in recent years, a highly precise radiotherapy device with a radiation beam resolution of 3 mm has been used.

The radiation beam solution refers to an ability to minimize radiation exposure to normal tissues other than cancer tissues by irradiating the radiation as precisely as possible during therapy.

In particular, in the head and neck radiation therapy, precision of the radiation therapy apparatus itself is also important, but it is necessary to securely fix the head and the neck to prevent damage to normal brain tissues around an affected area such as the tumor.

In general, a thermoplastic mask is used to fix the head of a patient in the therapy of head and neck tumors, and a thermal deformation mask is made to have strength within a range of fixability for fixing the head of the patient.

Additionally, a fixed belt for fixing other arms, legs, etc. of the body may be further used.

In the therapy of head and neck cancer using the radiation, a therapy plan is established with the head fixed by using the thermoplastic mask which is a therapeutic aid and the same aid is used even in actual therapy to make a therapy plan be the same as a patient state in the actual therapy.

However, when the mask is used for the head and neck cancer therapy, a space between the patient and the mask may cause the head of the patient to move inside the mask, and as a result, the radiation may be transferred to a different part from the therapy plan.

The precise therapy of the radiation therapy has a great impact on the life of the patient and inaccurate therapy leads to excessive destruction of normal cells, which may lead to adverse effects of patients and decrease quality of the life.

In particular, in the head and neck, many important organs are distributed in the body, so more effort is needed to make more accurate therapy.

In recent years, in the radiation therapy of the head and neck cancer, therapy attempts have been made using stereotactic radiosurgery (SRS) to reduce the fraction of radiation and to irradiate large amounts of radiation.

As the SRS becomes more and more widespread, patient movement and precise patient positioning become more important.

Therefore, in the radiation therapy of the head and neck cancer, required is a system which performs more accurate and safe radiation therapy than the case of applying only the thermoplastic mask in the related art by providing precise information on the same position as the patient's therapy plan and the patient's movement during the radiation therapy.

PRIOR ART DOCUMENT (Patent Document 0001) USPTO Laid-Open No. 20140153811 (application Ser. No. 13/693,406)

DISCLOSURE

Technical Problem

An object of the present invention is to provide a system for assisting confirming the movement of a head within a thermoplastic mask by using a pressure sensor and controlling the movement of the head, in therapy of head and neck cancer using radiation.

Specifically, in the present invention, the pressure sensor is positioned between the mask and the head and a signal of the pressure sensor is represented by a computer programmed system to confirm whether the movement occurs in the mask and support safe radiation therapy of a patient. Further, the radiation therapy may be discontinued when the intensity of the signal is significantly changed due to excessive movement during the therapy.

The technical objects of the present invention are not limited to the aforementioned technical objects, and other technical objects, which are not mentioned above, will be apparently appreciated by a person having ordinary skill in the art from the following description.

Technical Solution

In order to solve the technical problems, a thermoplastic mask according to an aspect of the present invention may include: a mask having a shape determined according to a shape of a first region which is at least a part of a patient's body by using thermoplasticity, fixing the first region in close contact with the first region, and receiving radiation; and a pressure sensor provided between the mask and the first region and sensing pressure induced by a space generated between the mask and the first region.

Further, the pressure sensor may further include a communication unit transmitting information on the sensed pressure to the outside.

In addition, the thermoplastic mask may further include a controller determining whether the first region is fixed through the mask by using a change in the sensed pressure.

In addition, the thermoplastic mask may further include a controller controlling the apparatus to stop an output operation of the radiation when the sensed pressure is more than a predetermined numerical value.

Meanwhile, in order to solve the technical problems, a system for monitoring a thermoplastic mask according to another aspect of the present invention may include: a mask having a shape determined according to a shape of a first region which is at least a part of a patient's body by using thermoplasticity and fixing the first region in close contact with the first region; an apparatus outputting radiation to the first region fixed by the mask; a pressure sensor provided between the mask and the first region and sensing pressure induced by a space generated between the mask and the first region; and a communication unit transmitting information on the pressure sensed by the pressure sensor to the outside.

In addition, the system for monitoring a thermoplastic mask may further include a controller determining whether the first region is fixed through the mask by using a change in the sensed pressure.

Further, the system for monitoring a thermoplastic mask may further include a controller controlling the apparatus to stop an output operation of the radiation when the sensed pressure is more than a predetermined numerical value.

Further, the first region may be at least a part of a head of the patient, and the apparatus may be an apparatus that outputs the radiation in association with head and neck cancer.

Further, the communication unit may adopt at least one of wired communication, short-range communication, and long-range communication, and the short-range communication may include ANT, Bluetooth, radio frequency identification (RFID), infrared data association (IrDA), and ultra wideband (UWB), ZigBee technologies and the long-range communication may include code division multiple access (CDMA), frequency division multiple access (FDMA), time division multiple access (TDMA), orthogonal frequency division multiple access (OFDMA), and single carrier frequency division multiple access (SC-FDMA).

In addition, the pressure sensor may include: a substrate; a differential pressure diaphragm installed at the center of the substrate; a first differential pressure gauge installed on the circumference of the differential pressure diaphragm and formed in a diameter direction to the center of the differential pressure diaphragm; a second differential pressure gauge interposed between the first differential pressure gauge and the differential pressure diaphragm and formed in a circumferential direction which is orthogonal to the diameter direction on the circumference of the differential pressure diaphragm; a third differential pressure gauge installed in the vicinity of the first differential pressure gauge on the circumference of the differential pressure diaphragm and installed in the circumferential direction; a fourth differential pressure gauge interposed between the third differential pressure gauge and the differential pressure diaphragm and formed in the diameter direction on the circumference of the differential pressure diaphragm; a first static pressure diaphragm installed on an outer portion of the differential pressure diaphragm and interposed between the third differential pressure gauge and the fourth differential pressure gauge in the circumferential direction; and second static pressure diagrams installed on the outer portion of the differential pressure diaphragm and disposed at opposed positions with the differential pressure diaphragm interposed therebetween.

Further, the pressure sensor may include a plurality of beams formed in lattice shape and having a wire groove at an intersection, a strain gauge attached to each of the plurality of beams to measure a strain, and a frame connected with the end of the lattice shape and covering the plurality of beams, and the beam may has a smaller thickness than the frame, and the beam may further include a support supporting the plurality of beams below the intersection of the plurality of beams, the wire groove may be formed to penetrate the intersection and the support, the sum of the thickness of the intersection and the thickness of the support may be equal to the thickness of the frame, and the support may be formed so that an area of a cross-section contacting the intersection is limited within the area of the intersection.

In addition, the pressure sensor may include a silicon die and a capacitor electrode, and the silicon die may include a vibratory diaphragm, the silicon die may have a silicon die top at an opposite side to a silicon die bottom, a top silicon die port may extend from the silicon die top to the top of the vibratory diaphragm through the silicon die, a bottom silicon die port may extend from the silicon die bottom to the bottom of the vibratory diaphragm, and the bottom silicon die port may have a larger cross-sectional area than the top silicon die port, the capacitor electrode may be positioned to pass through the bottom silicon die port along the bottom of the silicon die, and the capacitor electrode may include a first signal generating unit positioned throughout the same space as the top silicon die port and a second signal generating unit surrounding the first signal generating unit.

Meanwhile, in order to solve the technical problems, a method for monitoring a thermoplastic mask according to yet another aspect of the present invention may include: determining a shape of the mask according to the shape of a first region which is at least a part of a patient's body by using thermoplasticity; fixing, by the mask, the first region in close contact with the first region; outputting radiation to the first region fixed by the mask; sensing pressure induced by a space generated between the mask and the first region by using a pressure sensor provided between the mask and the first region; and transmitting information on the pressure sensed by the pressure sensor to the outside.

In addition, the method for monitoring a thermoplastic mask may further include determining whether the first region is fixed through the mask by using a change in the sensed pressure.

Further, the method for monitoring a thermoplastic mask may further include stopping, by the apparatus, an output operation of the radiation when the sensed pressure is more than a predetermined numerical value.

In addition, the first region may be at least a part of a head of the patient, and the radiation output to the first region may be associated with head and neck cancer.

Further, at least one of wired communication, short-range communication, and long-range communication may be used in order to transmit the information to the outside, and, and the short-range communication may include ANT, Bluetooth, radio frequency identification (RFID), infrared data association (IrDA), and ultra wideband (UWB), ZigBee technologies and the long-range communication may include code division multiple access (CDMA), frequency division multiple access (FDMA), time division multiple access (TDMA), orthogonal frequency division multiple access (OFDMA), and single carrier frequency division multiple access (SC-FDMA).

Advantageous Effects

The present invention can provide a system for assisting confirming the movement of a head within a thermoplastic mask by using a pressure sensor and controlling the movement of the head, in therapy of head and neck cancer using radiation.

Specifically, in the present invention, the pressure sensor is positioned between the mask and the head and a signal of the pressure sensor is represented by a computer programmed system to confirm whether the movement occurs in the mask and support safe radiation therapy of a patient. Further, the radiation therapy may be discontinued when the intensity of the signal is significantly changed due to excessive movement during the therapy.

Effects which can be obtained in the present invention are not limited to the aforementioned effects and other unmentioned effects will be clearly understood by those skilled in the art from the following description.

DESCRIPTION OF DRAWINGS

FIGS. 12A to 12C illustrate an embodiment of a pressure sensor according to the present invention.

FIGS. 13A to 13C illustrate another embodiment of the pressure sensor according to the present invention.

FIGS. 14A to 14D illustrate yet another embodiment of the pressure sensor according to the present invention.

BEST MODE

Prior to a detailed description of the present invention, a magnetic resonance imaging apparatus according to the present invention will be described in detail.

Figure 1:
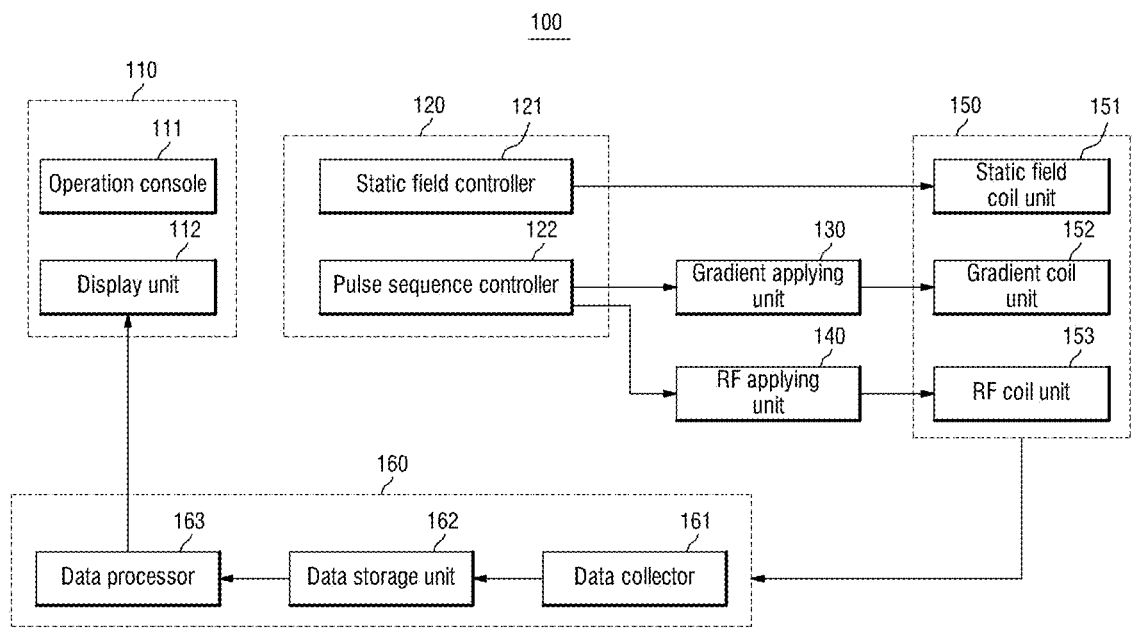
FIG. 1 illustrates an example of a control block diagram of a magnetic resonance imaging apparatus according to the present invention.

FIG. 1 illustrates an example of a control block diagram of a magnetic resonance imaging apparatus according to the present invention.

Referring to FIG. 1, a magnetic resonance imaging apparatus according to an embodiment of the present invention includes a bore 150 forming a magnetic field and generating a resonance phenomenon with respect to an atomic nucleus, a coil controller 120 controlling the operation of coils constituting the bore 150, an image processor 160 receiving an echo signal generated from the atomic nucleus to generate a magnetic resonance image, a workstation 110 controlling the overall operation of the magnetic resonance imaging apparatus, and the like.

The bore 150 includes a static field coil unit 151 forming a static field therein, a gradient coil unit 152 forming a gradient field in the static field, and an RF coil unit 153 exciting the atomic nucleus by applying an RF pulse and receiving an echo signal from the atomic nucleus.

The coil controller 120 includes a static field controller 121 controlling the strength and the direction of the static field formed by the static field coil unit 151 and a pulse sequence controller 122 designing a pulse sequence to control the gradient coil unit 152 and the RF coil unit 153.

The magnetic resonance imaging apparatus according to the embodiment of the present invention includes a gradient applying unit 130 applying a gradient signal to the gradient coil unit 152 and an RF applying unit 140 applying an RF signal to the RF coil unit 153.

The pulse sequence controller 122 controls the gradient applying unit 130 and the RF applying unit 140 to adjust the gradient field formed in the static field and the RF applied to the atomic nucleus.

Further, the magnetic resonance imaging apparatus according to the embodiment of the present invention includes the workstation 110 so that an operator of the magnetic resonance imaging apparatus may operate the apparatus to receive a control command for the overall operation of the magnetic resonance imaging apparatus 100.

The workstation 110 may include an operation consol 111 provided so that the operator operates the system and a display unit 112 which displays a control state and displays an image generated from the image processor 160 to allow the user to diagnose a health condition of a subject 200.

Figure 2:
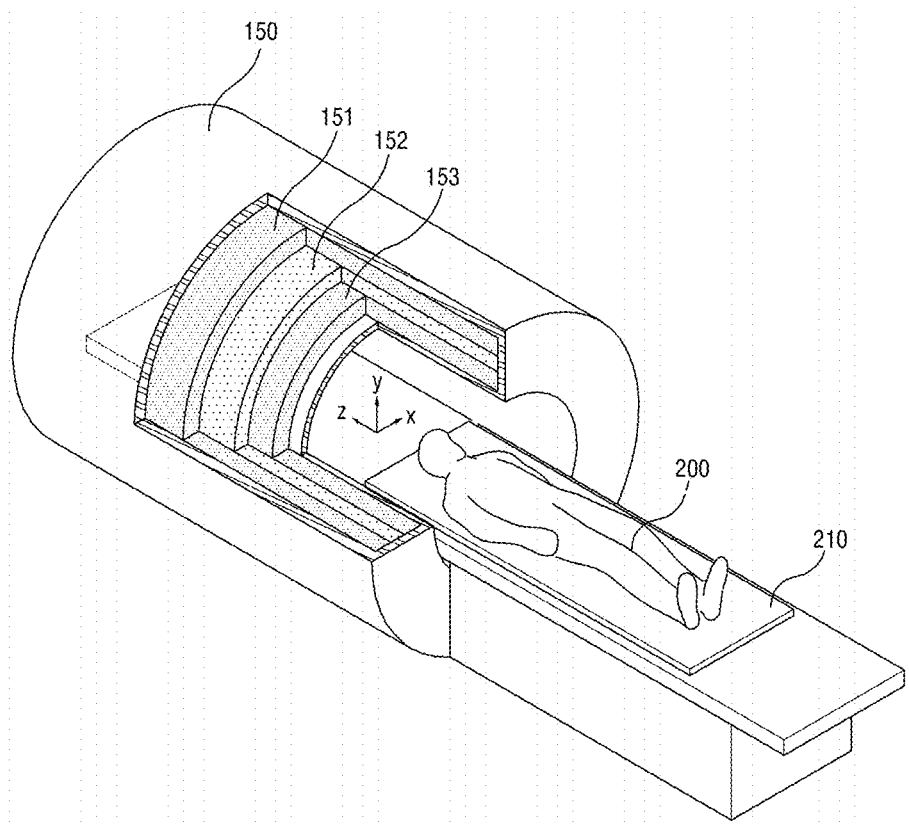
FIG. 2 is a view schematically illustrating an appearance of the magnetic resonance imaging apparatus according to the present invention.
Figure 3:
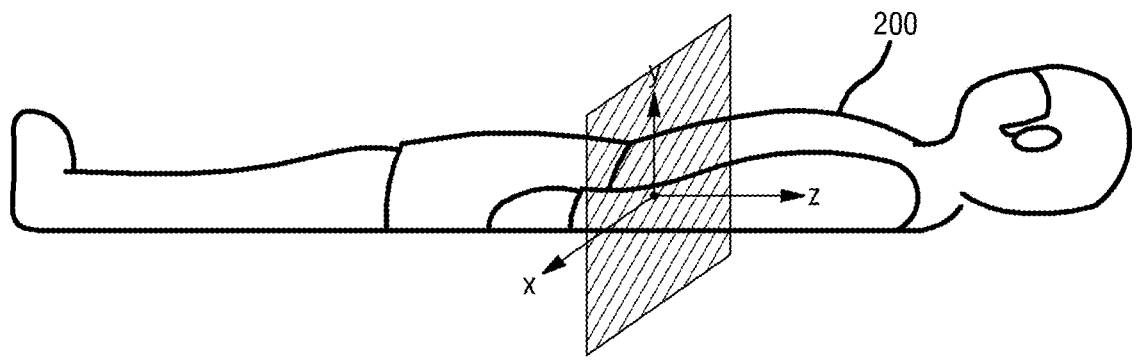
FIG. 3 is a view illustrating a space in which the subject is placed and which is divided into x, y and z axes.
Figure 4:
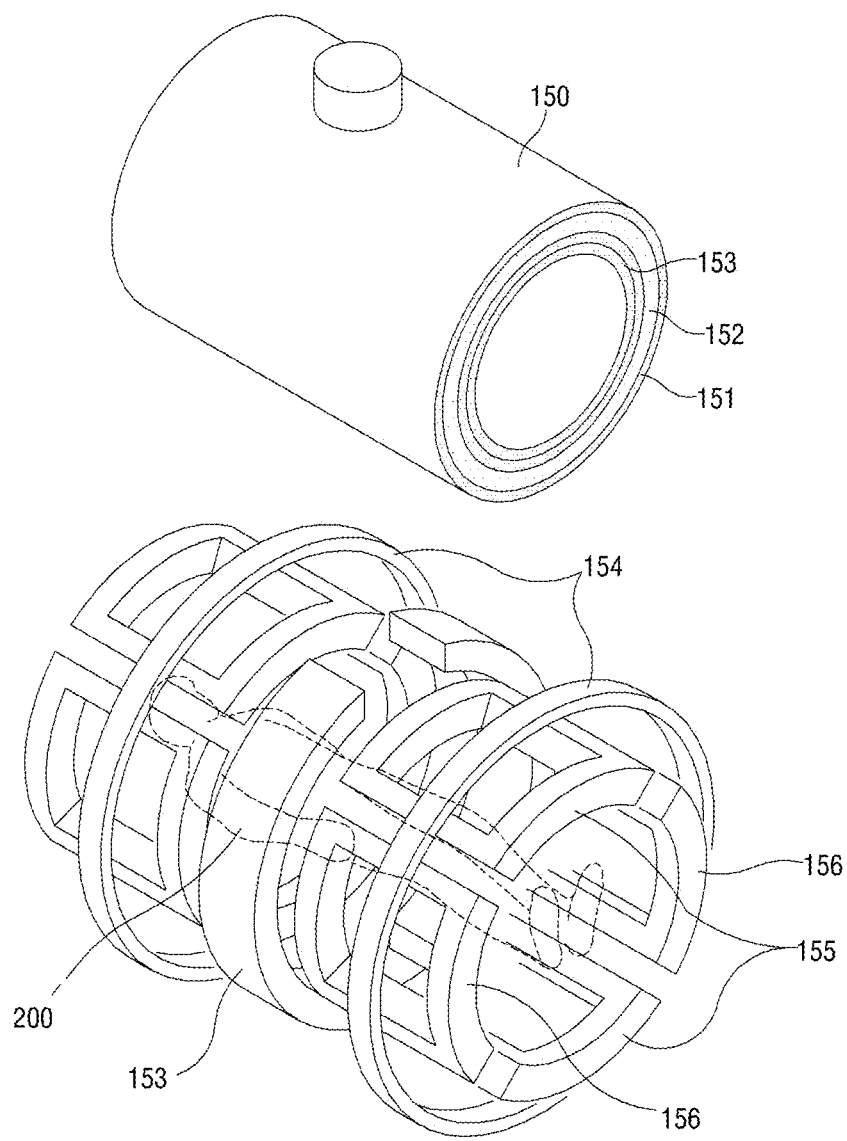
FIG. 4 is a view illustrating a structure of the bore and a structure of the gradient coil unit according to the present invention.
Figure 5:
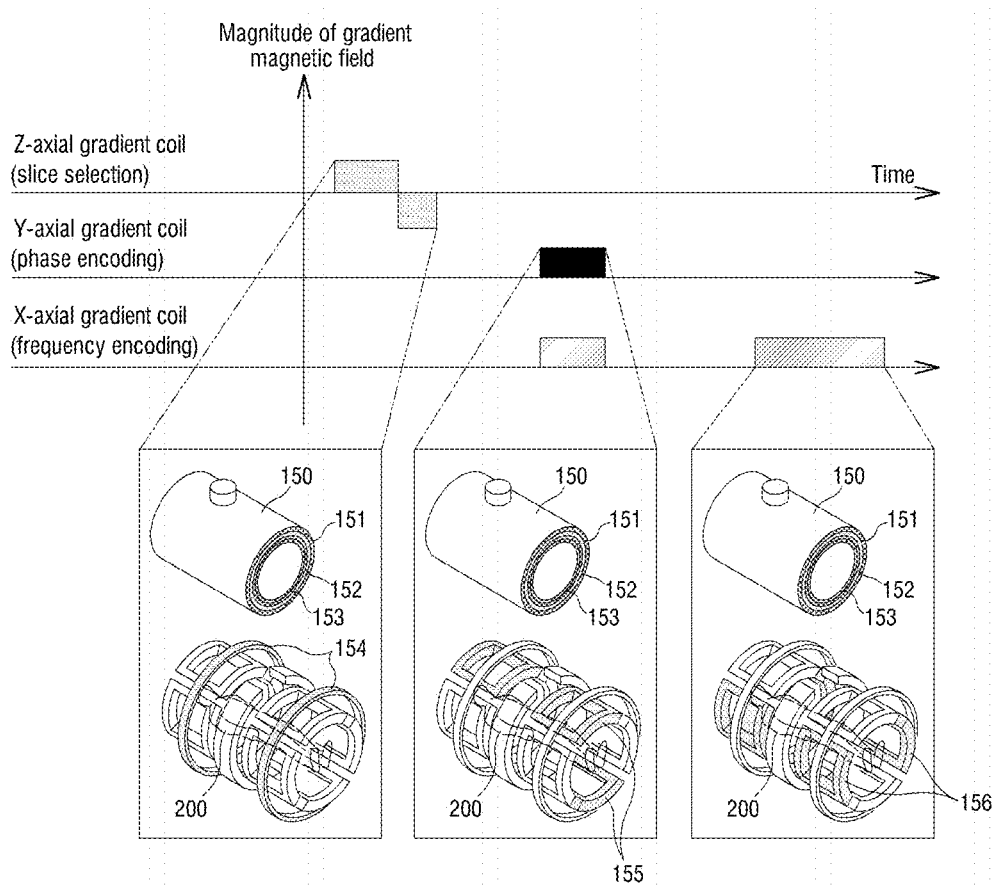
FIG. 5 is a view illustrating a pulse sequence related to each gradient coil constituting the gradient coil unit and the operation of each gradient coil.

Further, FIG. 2 is a view schematically illustrating an appearance of the magnetic resonance imaging apparatus according to the present invention. FIG. 3 is a view illustrating a space in which the subject is placed and which is divided into x, y and z axes, FIG. 4 is a view illustrating a structure of the bore and a structure of the gradient coil unit according to the present invention, and FIG. 5 is a view illustrating a pulse sequence related to each gradient coil constituting the gradient coil unit and the operation of each gradient coil.

Hereinafter, a detailed operation of the magnetic resonance imaging apparatus according to the embodiment of the present invention will be described with reference to FIG. 1 described above.

The bore 150 has a cylindrical shape in which an inner space is empty, and the inner space thereof is called a cavity portion.

A transfer unit transfers the subject 200 laid thereon to the cavity portion to obtain a magnetic resonance signal.

The bore 150 includes the static field coil unit 151, the gradient coil unit 152, and the RF coil unit 153.

The static field coil unit 151 may have a shape in which a coil is wound around the cavity portion, and the static field is formed inside the bore 150, that is, in the cavity portion when the current is applied to the static field coil unit 151.

The direction of the static field is generally parallel to the coaxial axis of the bore 150.

When the static field is formed in the cavity portion, atoms constituting the subject 200, particularly, atomic nuclei of hydrogen atoms are arranged in a direction of the static field and perform precession based on the direction of the static field. A precession rate of the atomic nuclei may be expressed by a precession frequency, which is called a Larmor frequency and may be expressed by the following Equation 1.

$$\Omega = \gamma B0 \quad \text{[Equation 1]}$$

Herein, $\Omega$ is a Larmor frequency, $\gamma$ is a proportional constant, and B0 is the intensity of an external magnetic field. The proportional constant varies according to a type of atomic nucleus, and a unit of the intensity of the external magnetic field is Tesla (T) or Gauss (G) and a unit of the precession frequency is Hz.

For example, a hydrogen proton has a precession frequency of 42.58 MHZ in an external magnetic field of 1 T, and since hydrogen occupies the largest proportion of the atoms constituting the human body, the magnetic resonance imaging apparatus uses the precession of the hydrogen protons to obtain a magnetic resonance signal.

The gradient coil unit 152 generates a gradient in the static field formed in the cavity portion to form a gradient magnetic field.

As illustrated in FIG. 3, an axis parallel to a vertical direction from the head to the foot of the subject 200, that is, an axis parallel to the direction of the static field may be determined as a z axis, an axis parallel to a horizontal direction of the subject 200 may be determined as an x axis, and an axis parallel to a vertical direction in the space may be determined as an y axis.

In order to obtain three-dimensional spatial information, the gradient magnetic field is required in all the x, y, and z axes. As a result, the gradient coil unit 152 includes three pairs of gradient coils.

As illustrated in FIGS. 4 and 5, the z-axial gradient coil 154 is generally constituted by a pair of ring-type coils, and the y-axial gradient coil 155 is located above and below the subject 200. The x-axial gradient coil 156 is located at left and right sides of the subject 200.

When a DC current having an opposite polarity flows in an opposite direction in each of the two z-axis gradient coils 154, a magnetic field is changed in the z-axial direction to form a gradient magnetic field. In FIG. 5, the z-axial gradient magnetic field formed when the z-axis gradient coils 154 operate is illustrated as the pulse sequence.

The z-axis gradient coils 154 are used for the selection of a slice and may select a slice having a small thickness as the slope of the gradient magnetic field formed in the z-axial direction is increased.

When the slice is selected through the gradient magnetic field formed by the z-axis gradient coils 154, spins constituting the slice has the same frequency and the same phase, and thus, each spin may not be distinguished.

In this case, when the gradient magnetic field is formed in the y-axial direction by the y-axial gradient coil 155, the gradient magnetic field causes a phase shift so that rows of the slice have different phases.

That is, when the y-axial gradient magnetic field is formed, the spins in the raw with a large gradient magnetic field are changed in phase to a high frequency and the spins in the raw with a small gradient magnetic field are changed in phase to a lower frequency.

When the y-axial gradient magnetic field is removed, the respective rows of the selected slice cause the phase shift or have different phases, thereby distinguishing the rows. As such, the gradient magnetic field generated by the y-axial gradient coil 155 is used for phase encoding.

In FIG. 5, the y-axial gradient magnetic field formed when the y-axial gradient coil 155 operate is illustrated as the pulse sequence.

The slice is selected through the gradient magnetic field formed by the z-axial gradient coil 154, and the rows constituting the slice selected by the gradient magnetic field formed by the y-axial gradient coil 155 are distinguished in different phases. However, since all the spins constituting the row have the same frequency and the same phase and thus, may not be distinguished from each other.

At this time, if the gradient magnetic field is formed in the x-axial direction by the x-axial gradient coil 156, the gradient magnetic field distinguishes each spin from each other so that the spins constituting each row have different frequencies.

As such, the gradient magnetic field generated by the x-axial gradient coil 156 is used for frequency encoding.

As described above, the gradient magnetic field formed by x, y, and z-axial gradient coils spatially encode spatial locations of the spins through slice selection, phase encoding, and frequency encoding.

The gradient coil unit 152 is connected with the gradient applying unit 130 and the gradient applying unit 130 applies a driving signal to the gradient coil unit 152 according to a control signal received from the pulse sequence controller 122 to generate a gradient magnetic field.

The gradient applying unit 130 may include three driving circuits corresponding to three gradient coils 154, 155, and 156 constituting the gradient coil unit 152.

As described above, atomic nuclei arranged by the external magnetic field perform the precession at a Larmor frequency and a magnetization vector sum of many atomic nuclei may be represented by one net magnetization M.

The z-axial component of the mean magnetization cannot be measured and only Mxy may be detected. Accordingly, in order to obtain the magnetic resonance signal, the mean magnetization needs to be present on an XY plane by exciting the atomic nuclei. For excitation of the atomic nuclei, the RF pulse tuned at the Larmor frequency of the atomic nuclei needs to be applied to the static field.

The RF coil unit 153 includes a transmission coil transmitting an RF pulse and a reception coil receiving an electromagnetic wave, that is, a magnetic resonance signal emitted by the excited atomic nuclei.

The RF coil unit 153 is connected with the RF applying unit 140 and the RF applying unit 140 applies a driving signal to the RF coil unit 153 according to a control signal received from the pulse sequence controller 122 to generate an RF pulse.

The RF applying unit 140 may include a modulation circuit modulating a high-frequency output signal into a pulse type signal and an RF power amplifier amplifying the pulse type signal.

The RF coil unit 153 is connected to the image processor 160, and the image processor 160 includes a data collector 161 which receives the magnetic resonance signal received by the RF coil unit 153 and processes the received magnetic resonance signal to generate a magnetic resonance image and a data processor 163 which processes data generated by the data collector 161 to generate a magnetic resonance image.

The data collector 161 includes a preamplifier amplifying the magnetic resonance signal received by the receiving coil of the RF coil unit 153, a phase detector receiving the magnetic resonance signal from the preamplifier and detecting the phase, and an A/D converter converting an analog signal obtained by the phase detection into a digital signal. In addition, the data collector 161 transmits the digital-converted magnetic resonance signal to a data storage unit 162.

A data space constituting a two-dimensional Fourier space is formed in the data storage unit 162, and when the scanned overall data is stored, the data processor 163 performs two-dimensional inverse Fourier transform on the data in the two-dimensional Fourier space to reconfigure the image for the subject 200. The reconfigured image is displayed on a display 112.

There is a spin-echo pulse sequence that is commonly used to obtain magnetic resonance signals from the atomic nuclei. When the RF pulse is applied in the RF coil unit 153, if the RF pulse is transmitted once again with an appropriate time interval $^\Delta T$ after the first RF pulse is applied, strong transverse magnetization appears in the atomic nuclei when a time $^\Delta t$ elapses from this to obtain a magnetic resonance signal.

This is called a spin-echo pulse sequence and the time taken until the magnetic resonance signal is generated after applying the first RF pulse is called a time echo (TE).

How many the protons are flipped may be represented by angles that are shifted from the axis located before the flip and represented by a 90° RF pulse or a 180° RF pulse depending on the flip degree.

Generally, the magnetic resonance imaging apparatus is used for determining anatomical structures of the human body to diagnose diseases, but in recent years, attempts to express functions performed by human organs, particularly, a brain function by an image have been continuously made and this is called a functional MRI (fMRI, hereinafter, referred to as a functional magnetic resonance imaging method).

The brain has a unique function in each region, and in order to perform a specific function, it is known that as brain activity of a specific site increases, local cerebral blood flow and metabolism of the specific region increase. The functional MRI expresses the location of the function by an image after inducing local neuronal activity in the brain by using these physiological changes. The functional MM has excellent spatial and temporal resolution as compared with a position emission tomography (PET) and can be repetitively performed without requiring injection of isotope.

The functional MRI has various methods, but a blood oxygen level-dependent (BOLD) method is most commonly used. The increase in local blood flow according to the activity of the brain means an increase in oxygen amount supplied to the activated brain tissue, and in this case, the increased oxygen supply amount increases an amount of oxyhemoglobin in capillaries and veins to relatively reduce the concentration of deoxyhemoglobin.

Since the deoxyhemoglobin is a paramagnetic material that shortens the T2 relaxation time therearound, a decrease in the material causes an increase in signal on a T2 enhanced image.

On the other hand, when a patient moves during the scanning of the functional magnetic resonance image, artifacts are generated in the functional image obtained by the functional magnetic resonance imaging method.

Unlike other organs, the brain is rarely changed in shape during scanning, and the entire shape of the brain moves in one direction or up, down, left, and right by the motion of the patient or only the rotating motion is shown.

Currently, radiation therapy is widely used for diagnosis and treatment of cancer, but in the case of radiation therapy, a large amount of radiation dose is generated to have a great effect on the patient. For example, radiation has various effects, such as DNA change, cancer induction, vomiting and headache depending on the dose.

Thus, efforts to reduce the amount of dose to patients are being made worldwide. For example, a method of treating liver cancer includes liver transplantation, resection surgery, percutaneous alcohol injection, radiofrequency thermal ablation, and the like. The radiofrequency thermal ablation (RFA) is a therapy method of burning and removing cancer cells with heat generated by a high frequency without surgery.

Meanwhile, the configuration of the present invention may be applied even to a method of detecting cancer using the PET and the RFA.

Figure 6:
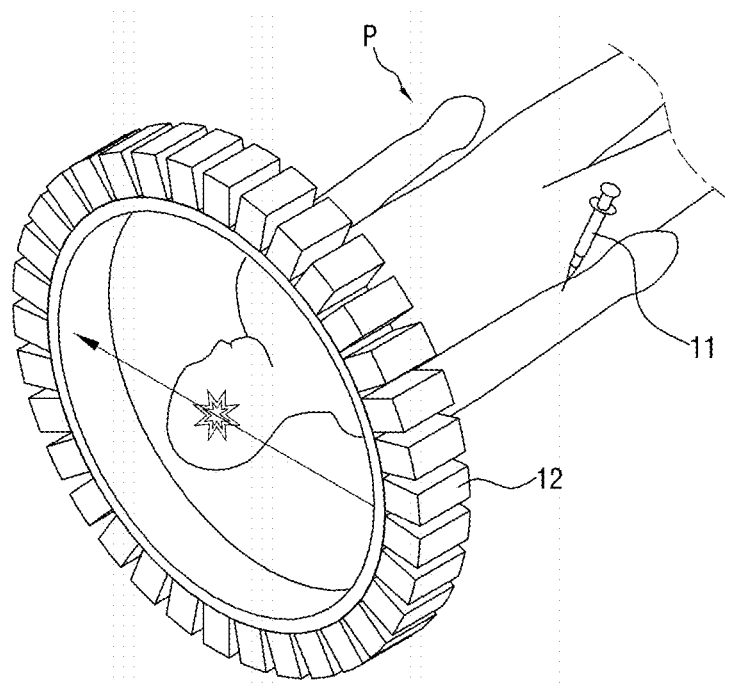
FIG. 6 is a diagram illustrating cancer detection using the PET and FIG. 7 is a diagram illustrating cancer therapy using the RFA.
Figure 7:
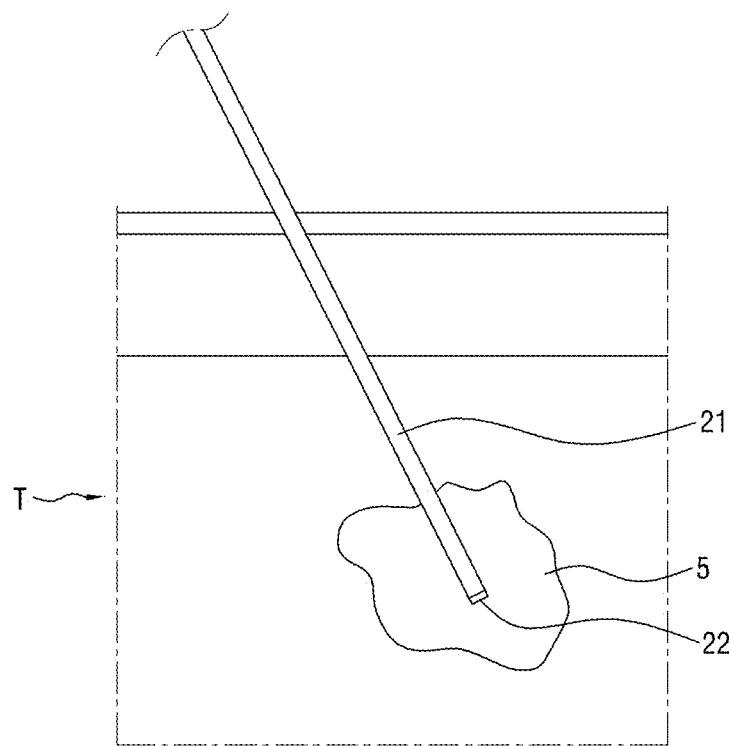

FIG. 6 is a diagram illustrating cancer detection using the PET and FIG. 7 is a diagram illustrating cancer therapy using the RFA.

Referring to FIG. 6, the PET is referred to as positron emission tomography and diagnoses the abnormality of metabolism by photographing a metabolic process. After a drug combining radioactive isotopes emitting positron is injected (11) to the human body P, the drug combining radioactive isotopes is tracked using a detector 12 to determine distribution in the body. These PET devices have high specificity and sensitivity to cancer. However, in the case of the PET, radiation is used for a scan time for obtaining cancer information (location, size, etc.). In addition, the radiation is used even during radiation therapy (RT) for cancer therapy detected by the PET.

Referring to FIG. 7, the RFA is a therapy method for inserting an electrode 21 into a human tissue T and generating a high frequency therefrom to burn and remove cancer cells 5 with heat 22 generated therefrom.

Figure 8:
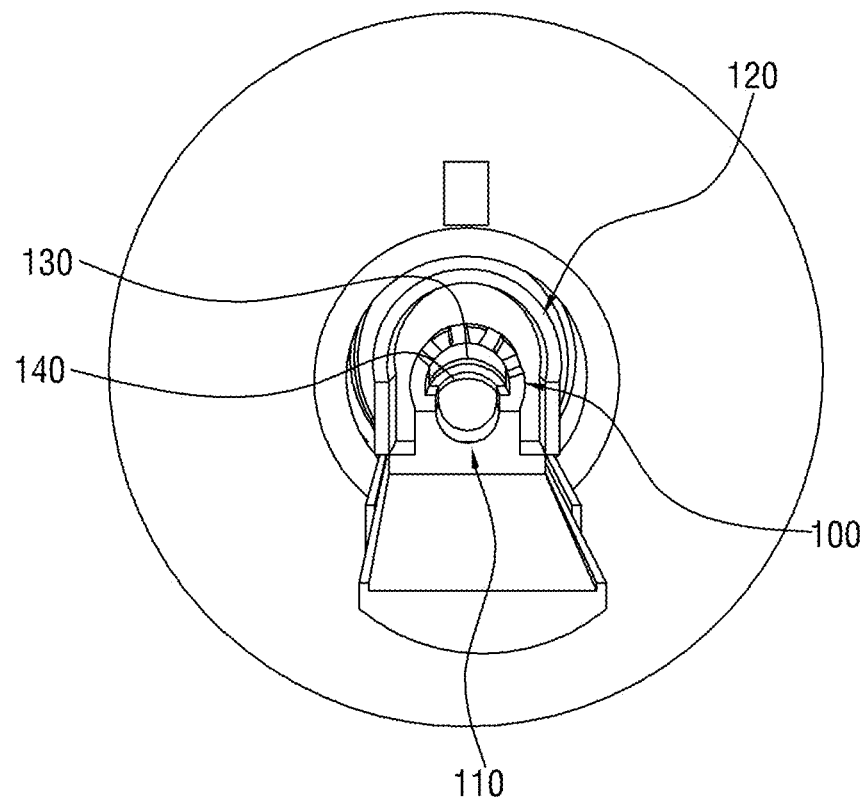
FIG. 8 is a configuration diagram of an apparatus of acquiring a PET image according to a preferred embodiment of the present invention.

Meanwhile, FIG. 8 is a configuration diagram of an apparatus of acquiring a PET image according to a preferred embodiment of the present invention.

Referring to FIG. 8, the apparatus of acquiring the PET image according to the exemplary embodiment includes an RF coil unit 100, a bed unit 110, a first PET detection unit 120, a second PET detection unit 130, and a collimator 140.

The RF coil unit 100 transits a radio wave generated by a frequency synthesizer. The radio wave is required for inducing a resonance phenomenon. The RF coil unit 100 adjusts a wavelength to select a resonance frequency of the nucleus and absorbs the adjusted signal in the resonant positron. At this time, when the RF power is interrupted, the excited atomic nucleus induces a current in the RF coil unit 100, and generates a weak RF signal.

The RF coil unit 100 is a configuration requiring for obtaining an Mill image, and when a CT scanner is included instead of the RF coil unit 100, a CT image may be obtained. Accordingly, the present invention may be utilized by a PET-CT apparatus or a PET-MM apparatus.

The bed unit 110 is a device which is located in the MM and on which a subject is placed.

The first PET detection unit 120 and the second PET detection unit 130 are devices constituting images using positron emitted from the radioactive isotope. The positron emitted from the radioactive isotope is emitted from the human body and then consumes kinetic energy itself for the shortest time, and disappears when coupling neighboring electrons, and emits two annihilation radiation rays (gamma ray) at an angle of 180°.

The first PET detection unit 120 is a device capable of detecting the two annihilation radiation rays emitted at the same time. In this case, the first PET detection unit 120 according to the embodiment of the present invention is configured by a curved PET detector having a curved cross section of a part of the first PET detection unit 120 located at a predetermined distance in a normal direction of one surface of the bed unit 110. In addition, the PET detectors are formed at both sides of the bed unit 110 and other parts of the first PET detection unit 120 formed vertically on one surface of the bed unit 110 may face each other. Accordingly, the cross section of the first PET detection unit 120 entirely has an ∩ shape or Ω shape. The reason why the cross section of the first PET detection unit 120 has the ∩ shape is that it is difficult to detect the radiation incident from the opposite side of the bed unit 110 on which the subject is placed by the bed unit 110.

That is, the first PET detection unit 120 according to the present invention may be configured such that while the RF coil unit 100 is mounted, the radiation is incident in pairs by the PET detectors facing each other, or the radiation is incident in pairs by any one of the PET detectors facing each other and the curved PET detector. That is, since the curved PET detector in the first PET detection unit 120 does not have the PET detector located below the bed unit 110 on which the corresponding subject is placed, the radiation is incident in pairs by any one of the PET detectors facing each other and the circular PET detector.

Also, the first PET detection unit 120 may acquire a PET image in a fixed state without rotation of a PET gantry.

The first PET detection unit 120 is installed on the bed unit 110 together with the RF coil unit 100, and the detectors are arranged in a round shape according to the curvature of the RF coil unit 100 without using the detectors arranged in a plane.

Meanwhile, the first PET detection unit 120 is not installed in the RF coil unit 100, but installed outside in a radial direction of the RF coil unit 100. The first PET detection unit 120 may use a semiconductor sensor so as not to be affected by the MRI magnetic field.

The second PET detection unit 130 is separately installed at a location in the normal direction of the cross section of the first PET detection unit 120 through which the subject passes.

Since there is no PET detector on the opposite side corresponding to the second PET detection unit 130, an image is formed using only one radiation which does not make a pair. In this case, the second PET detection unit 130 uses only the radiation in a specific direction which passes through the collimator 140 to configure the image even using only one radiation. The data generated by the second PET detection unit 130 may enhance the sensitivity of the PET detection unit by supplementing the data generated by the first PET detection unit 120.

In the PET detection unit described above, the first PET detection unit 120 generates a coincidence counting and the second PET detection unit 130 detects gamma ray using the collimator 140 and generates a single photon counting.

The collimator 140 is a device in which gamma ray coming in a specific direction is incident from a measurement site of the subject. The collimator 140 is formed in a hole having any one of various shapes such as a parallel line, a quadrangle, a hexagon, or a circle. The collimator 140 according to the present invention passes the radiation incident in the specific direction among the radiations incident to the second PET detection unit 130.

The collimator 140 passes gamma ray that is incident vertically to the cross section of the hole among the gamma rays emitted from the subject and the gamma ray in a predetermined angle to the vertical line of the hole cross section and blocks the gamma ray coming in the other direction. That is, the collimator 140 is a device in which only the gamma ray emitted from a required site is incident to a scintillation crystal by geometrically limiting the gamma ray emitted from the subject site. Accordingly, in the present invention, the image may be reconfigured using the gamma ray obtained at a limited angle by using the collimator 140. In particular, the gamma ray is acquired to a region where the coincidence counting cannot be generated by using the collimator 140 and then the image is reconfigured using the single photon counting.

The first PET detection unit 120 may include a scintillation crystal and the second PET detection unit 130 may include a scintillation crystal for detecting a gamma ray incident to the collimator 140, and the scintillation crystal may contact the incident gamma ray to generate a visible ray. Also, the first PET detection unit 120 and the second PET detection unit 130 may include a semiconductor sensor and a photomultiplier tube (PM tube), and the PM tube may convert the visible ray into photoelectrons which are electric signals to multiply the converted photoelectrons to a detectable signal.

Meanwhile, the configuration of the present invention may be applied even to a CT device.

Figure 9:
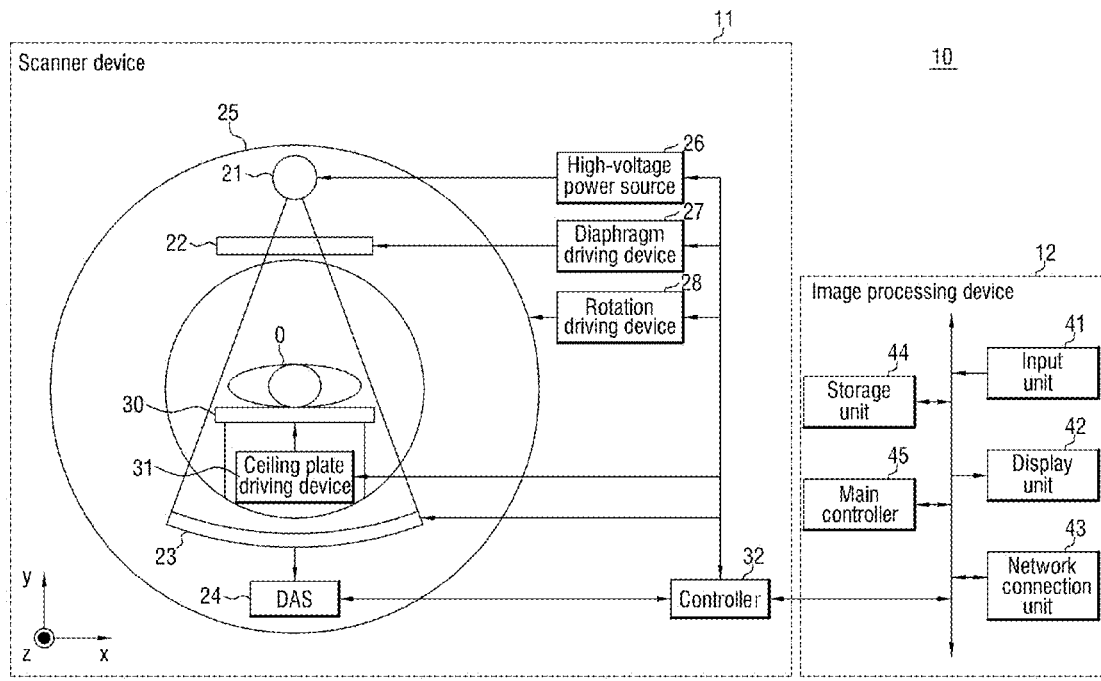
FIG. 9 is a schematic overall configuration diagram illustrating an example of a photon counting type X-ray CT apparatus according to an embodiment of the present invention.

FIG. 9 is a schematic overall configuration diagram illustrating an example of a photon counting type X-ray CT apparatus according to an embodiment of the present invention.

A photon counting type X-ray CT apparatus 10 has a scanner device 11 and an image processing device 12 as illustrated in FIG. 9.

The scanner device 11 of the X-ray CT apparatus 10 is generally installed in a laboratory to generate transmission data of the X ray on a region (subject) of a patient O. The image processing device 12 is generally installed in a control room adjacent to the laboratory and generates projection data from the transmission data to generate and display a reconfiguration image.

The scanner device 11 of the X-ray CT apparatus 10 includes an X-ray tube 21, an diaphragm 22, a photon counting type X-ray detector 23 (hereinafter, referred to as an X-ray detector), a data acquisition system (DAS) 24, a rotation unit 25, a high-voltage power source 26, an diaphragm driving device 27, a rotation driving device 28, a ceiling plate 30, a ceiling plate driving device 31, and a controller 32.

The generated X ray is irradiated toward the patient O as a fan beam X ray or a corn beam X ray.

The diaphragm 22 is controlled by the controller 32 through the diaphragm driving device 27 and adjusts an irradiation range in a slice direction of the X ray irradiated from the X-ray tube 21.

The X-ray detector 23 is configured by one or a plurality of X-ray detection elements (charge accumulating elements). The X-ray detection element detects the X ray irradiated from the X-ray tube 21. The X-ray tube 21 and the X-ray detector 23 are supported to the rotation unit 25 so as to face each other with the patient O placed on the ceiling plate 30 interposed therebetween.

As the X-ray detector 23, in the case of a multi-slice type, a plurality of rows of X-ray detection elements having a plurality of channels in a channel direction (X axis) may be arranged and used in the slice direction (Z axis). Also, in the case of a two-dimensional array type, the X-ray detector 23 may be constituted by a plurality of X-ray detection elements arranged in a densely distributed manner in both the channel direction (X axis) and the slice direction (Z axis).

The DAS 24 amplifies the transmission data signal detected by the X-ray detection element constituting the X-ray detector 23 to convert and output the amplified signal into a digital signal. Output data of the DAS 24 is given to the image processing device 12 through the controller 32 of the scanner device 11.

The rotation unit 25 integrally maintains the X-ray tube 21, the diaphragm 22, the X-ray detector 23, and the DAS 24. The rotation unit 25 is controlled by the controller 32 through the rotation driving device 28 to rotate and thus, the X-ray tube 21, the diaphragm 22, the X-ray detector 23, and the DAS 24 are integrally rotated around the patient O.

The high-voltage power source 26 is controlled by the controller 32 to supply the power required for irradiating the X ray to the X-ray tube 21. Information on a timing and period when the X-ray tube 21 generates the X ray, and a tube current and tube voltage to be applied to the X-ray tube 21 is given from the image processing device 12 to the controller 32.

The diaphragm driving device 27 is controlled by the controller 32 to adjust the aperture of the diaphragm 22 and adjust the irradiation range in the slice direction of the X-ray.

The rotation driving device 28 is controlled by the controller 32 to rotate the rotation unit 25 around the cavity portion.

The ceiling plate driving device 31 of the ceiling plate 30 is controlled by the controller 32 to move up the ceiling plate 30 in the Y-axial direction. Further, the ceiling plate driving device 31 is controlled by the controller 32 to transfer the ceiling plate 30 in the Z-axial direction in an X-ray irradiation field of the opening portion at the central portion of the rotation unit 25.

The controller 32 is constituted by storage media including a CPU, a RAM, and a ROM, and the scanning is executed by controlling the X-ray detector 23, the DAS 24, the high-voltage power source 26, the diaphragm driving device 27, the rotation driving device 28, and the ceiling plate driving device 31 according to programs stored in the storage media. The RAM of the controller 32 provides a work area for temporarily storing programs and data executed by the CPU. The storage media including the ROM of the controller 32 stores an activation program of the scanner device 11, a control program of the scanner device 11, and various data required for executing these programs.

Also, the storage media including the ROM of the controller 32 has a configuration including a recording medium readable by a CPU such as a magnetic or optical recording medium or a semiconductor memory, and a part or all of programs and data in these storage media may be configured to be downloaded through an electronic network.

On the other hand, the image processing device 12 of the photon counting type X-ray CT apparatus 10 is constituted by, for example, a personal computer, and may transmit and receive data with a network such as a local area network (LAN) in the hospital.

The image processing device 12 has an input unit 41, a display unit 42, a network connection unit 43, a storage unit 44, and a main controller 45 as illustrated in FIG. 9.

The input unit 41 is constituted by general input devices such as a keyboard, a trackball, a touch panel, a ten key, and the like, and outputs an operation input signal corresponding to the operation of the user to the main controller 45. For example, when a scan plan is set by the user through the input unit 41, the main controller 45 instructs, for example, the irradiation timing and period of the X-ray and the tube current and the tube voltage to be applied to the X-ray tube 21 to the controller 32 based on the scan plan. In addition, the controller 32 instructs the high-voltage power source 26 to supply the power to the X-ray tube 21 as the instructed tube current and tube voltage in the irradiation timing and irradiation period instructed by the main controller 45.

The display unit 42 is constituted by a general display output device such as a liquid crystal display or an organic light emitting diode (OLED) display and displays various images such as an image for each energy bin according to the control of the main controller 45.

The network connection unit 43 installs various information communication protocols according to a type of network. The network connection unit 43 connects other electric devices such as an image server with the image processing device 12 according to various protocols. As the connection, electric connection through the electronic network and the like may be applied.

Herein, the electronic network means the overall information communication network using a telecommunication technology. In addition to the wireless/wired LAN such as the hospital LAN or the Internet network, the electronic network includes a telephone communication network, an optical fiber communication network, a cable communication network, a satellite communication network, and the like.

The storage unit 44 has a configuration including a recording medium readable and writable by a CPU of the main controller 45, such as a magnetic or optical recording medium or a semiconductor memory, and a part or all of programs and data in these storage media may be configured to be downloaded through an electronic network. The storage unit 44 stores, for example, data collected by the scanner device 11, information associating the lesion with the energy width, information associating the site with the energy width, and the like.

The main controller 45 is constituted by a storage media, such as a CPU, a RAM, and a ROM, and controls the controller 32 of the scanner device 11 according to a scanner device control program stored in the storage media.

The CPU of the main controller 45 loads an EL/EW changing program stored in the storage media such as a ROM and data required for executing the program into the RAM, and executes a process of generating an image in real time to the change according to the program while changing the width of the energy bin according to the input operation of the user.

The RAM of the main controller 45 provides a work area for temporarily storing programs and data executed by the CPU. The storage media including the ROM of the main controller 45 stores an EL/EW changing program or various data required for executing the program.

Also, the storage media including the ROM has a configuration including a recording medium readable by a CPU, such as a magnetic or optical recording medium or a semiconductor memory, and a part or all of programs and data in these storage media may be configured to be downloaded through an electronic network.

Meanwhile, a thermoplastic mask for fixing the patient in a radiotherapy apparatus will be described in detail using FIG. 10.

Figure 10:
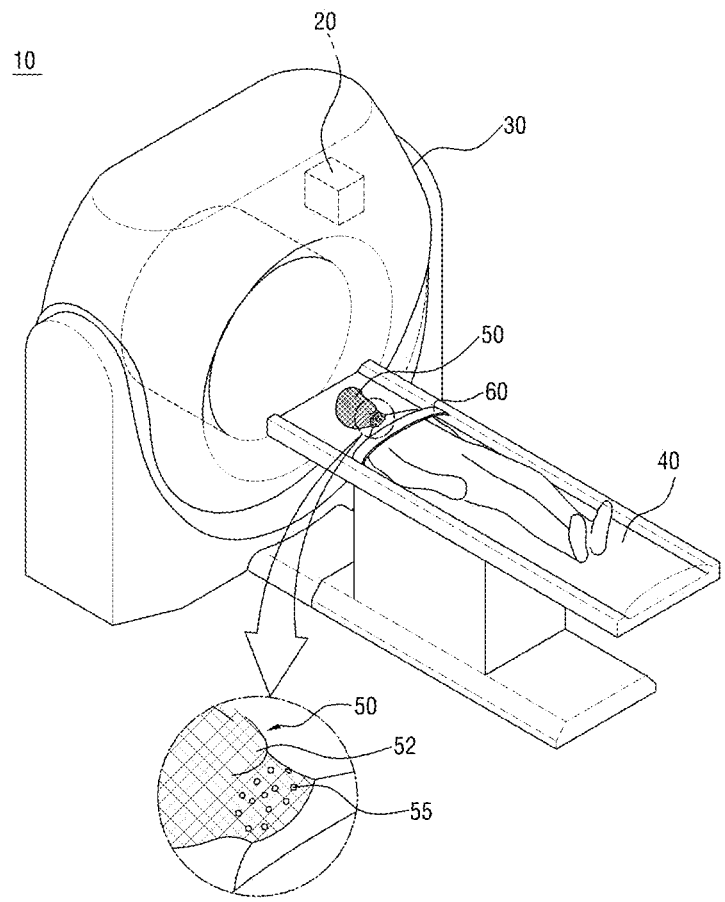
FIG. 10 illustrates a state diagram of a patient which wears a thermoplastic mask and a fixing belt for fixing the patient in a radiotherapy apparatus according to the present invention.

FIG. 10 illustrates a state diagram of a patient which wears a thermoplastic mask and a fixing belt for fixing the patient in a radiotherapy apparatus according to the present invention, which has the same basic configurations as the apparatus described in FIGS. 1 to 5, but has at least partially deformed form.

Figure 11:
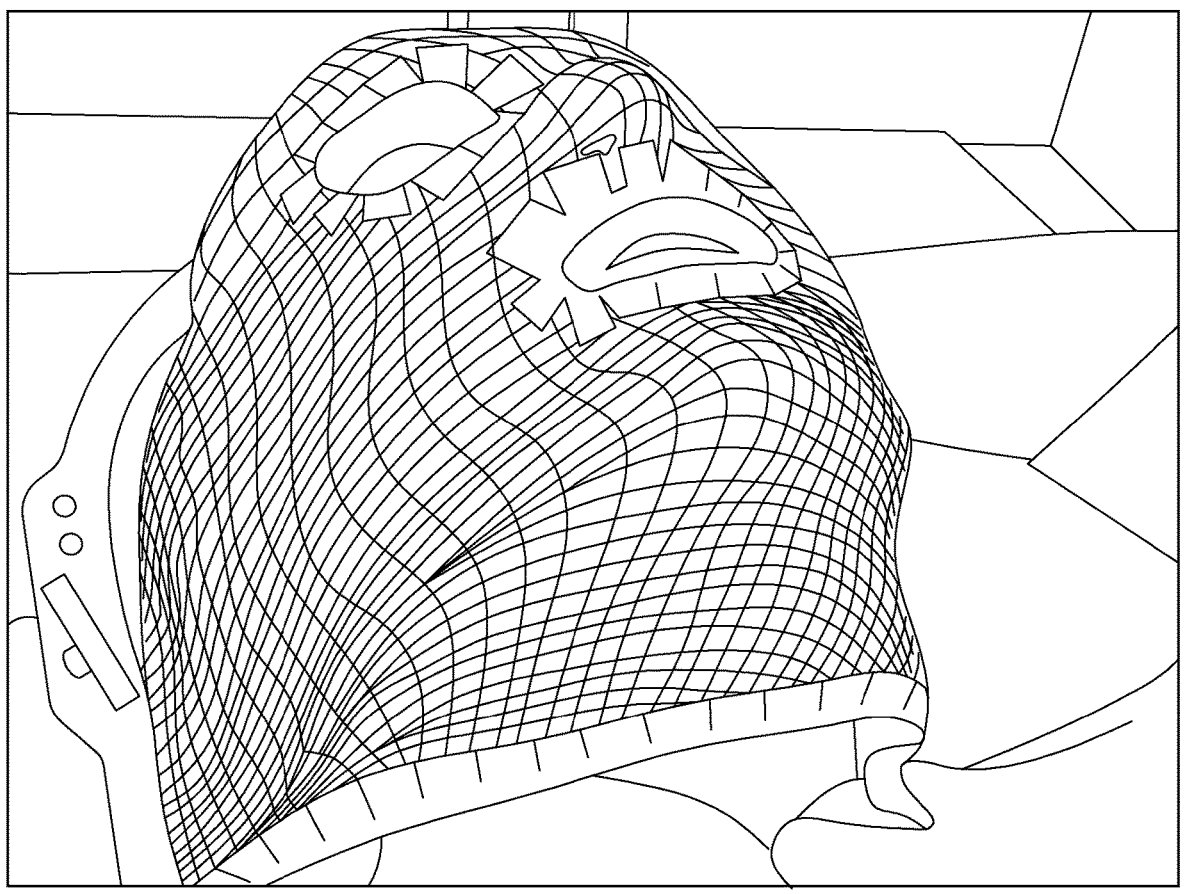
FIG. 11 illustrates a detailed example of the thermoplastic mask for fixing the patient in the radiotherapy apparatus according to the present invention.

Also, FIG. 11 illustrates a detailed example of the thermoplastic mask for fixing the patient in the radiotherapy apparatus according to the present invention.

Referring to FIG. 10, a radiotherapy apparatus 10 according to the present invention may include a radiation source 20, a gantry 30, and a treatment table 40.

The radiation source 20 generates radiation and is mounted on the gantry 30 disposed around the treatment table 40.

However, head and neck radiotherapy requires a very precise radiotherapy device because a treatment object itself is a very sensitive part of the body, and recently, a highly precise radiotherapy device with a beam resolution of about 3 mm has been used.

The beam resolution refers to the ability to minimize a radiation dose to normal tissues other than cancer tissues by irradiating the radiation as precisely as possible during treatment.

In particular, in the head and neck radiotherapy, the precision of the radiotherapy apparatus itself is important, but it is necessary to accurately fix the head and the neck to prevent damage on a normal brain tissue around the affected area such as the tumor.

Generally, a thermoplastic mask 50 is used to fix the head of a patient in the treatment of head and neck tumors, and the thermoplastic mask is fabricated to have the strength within a range of fixability for fixing the head of the patient.

In addition, a fixing belt 60 for fixing other arms, legs, etc. of the body may further be used.

Meanwhile, thermoplasticity applied to the thermoplastic mask will be described.

The thermoplasticity is a property of permanent deformation caused by the action of heat and force.

All fibers have the thermoplasticity somewhat.

All of the fibers are somewhat thermoplastic to be ironed.

In particular, chemical fibers such as triacetate, nylon, polyester and polypropylene have very good thermoplasticity.

Therefore, if these fibers or fiber products are shaped at a temperature slightly lower than the melting point of the fibers, the shape of the fibers is not deformed by washing or ironing, and this is called a heat set.

Polyester pleated skirts, nylon stockings, and stretch yarn are good examples of the heat set.

The thermoplasticity is a property which causes plastic change when heating and is reversibly cured when cooling. The thermoplasticity may be shown in synthetic resins (thermoplastic resins) made of chain polymers as well as metals, glass, etc.

The more remarkable the increase in fluidity due to heating, the higher the thermoplasticity.

Referring to FIG. 11, a detailed example of the thermoplastic mask for fixing the patient in the radiotherapy apparatus using the above-described thermoplasticity is illustrated.

Meanwhile, in the treatment of head and neck cancer using radiation, a therapy plan is established with the head fixed by using the thermoplastic mask, which is a therapeutic aid, and the patient conditions in the therapy plan and the actual treatment are made to be the same as each other using the therapeutic aid even in the actual treatment.

However, when the mask is used for the treatment of head and neck cancer, due to a space between the patient and the mask, the head of the patient may move inside the mask, and as a result, there is a problem in that the radiation may be transferred to a different part from the therapy plan.

Accurate treatment in radiotherapy has a great effect on the patient's life, and inaccurate treatment causes excessive destruction of normal cells to cause side effects and poor quality of life of the patient.

Particularly, in the head and neck, many important organs of the body are distributed, so more efforts are needed to make more accurate treatment.

Recently, in the radiotherapy of head and neck cancer, attempts for treatment using stereotactic radiosurgery (SRS) have been made to reduce the fractionation of radiation and to irradiate large amounts of radiation.

As the SRS is gradually enlarged, the movement and precise location of the patient become more important.

Accordingly, in the radiotherapy of head and neck cancer, a system of performing accurate and safe radiotherapy is required as compared with the conventional thermoplastic mask by providing precise information about the same position as the patient's therapy plan and the patient's movement which may occur during radiotherapy.

In order to solve this problem in the present invention, in the treatment of head and neck cancer using radiation, there is provided a system for confirming the movement of the head in the thermoplastic mask using a pressure sensor and helping in controlling the movement of the head.

Specifically, the present invention may confirm whether the movement occurs in the mask and support safe radiotherapy of the patient by positioning a pressure sensor between the mask and the head and expressing a signal of the pressure sensor in a computer programmed system. Further, the radiotherapy may also be interrupted if the intensity of the signal is largely changed due to excessive motion during treatment.

Before describing a detailed operation of the present invention, the pressure sensor applied to the system proposed by the present invention will be described in detail.

Pressure Sensor—First Embodiment

Figure 12B:
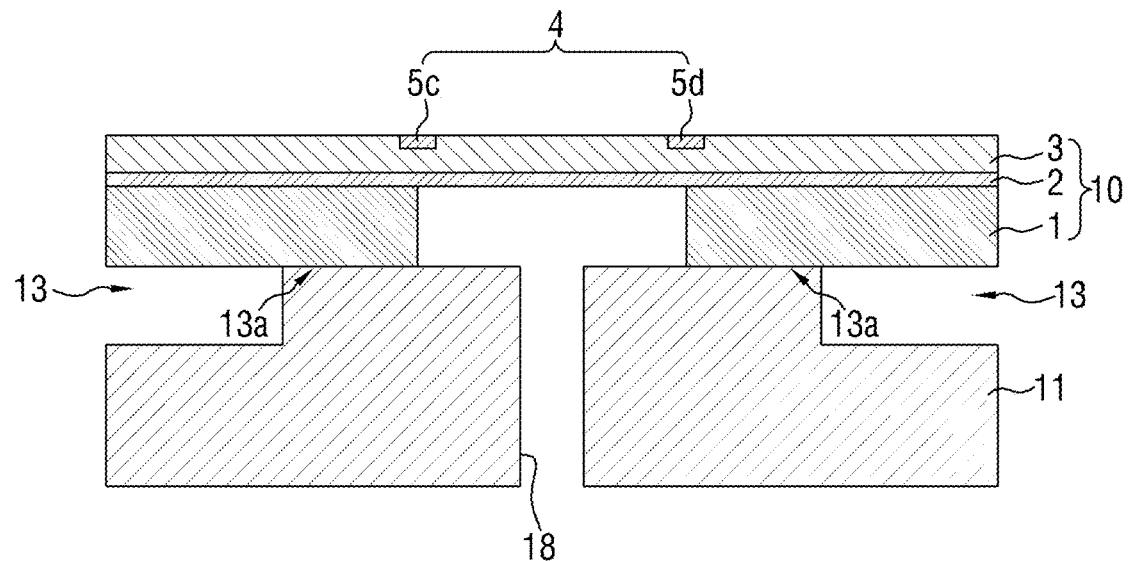
Figure 12C:
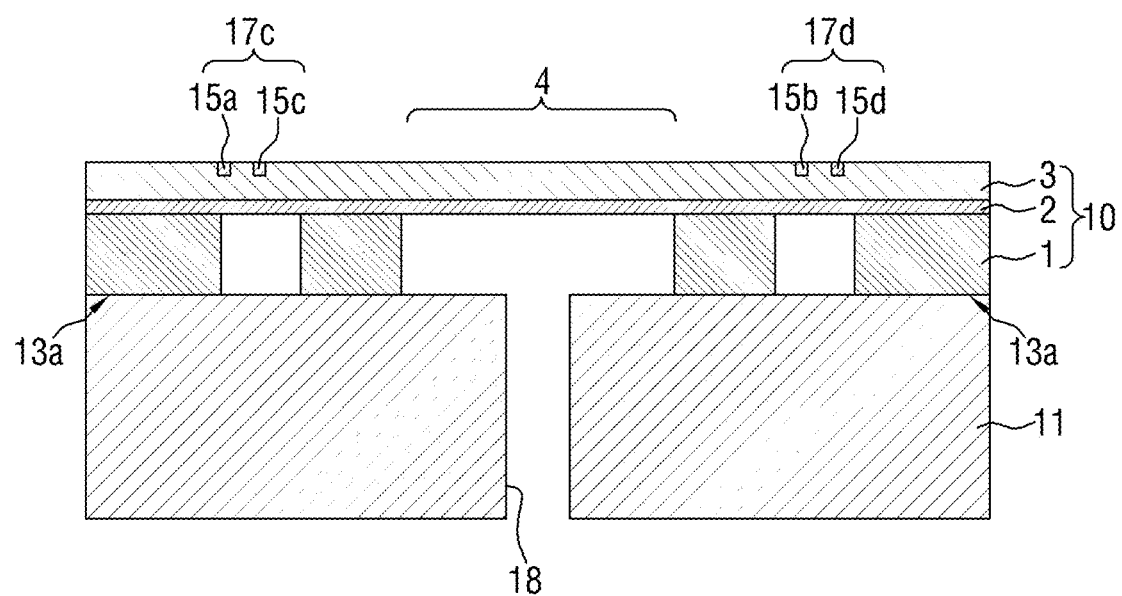

FIGS. 12A to 12C illustrate an embodiment of a pressure sensor according to the present invention.

It is assumed that the reference numerals illustrated in FIGS. 12A to 12C are independent from other drawings.

Referring to FIG. 12A, the pressure sensor applied to the present invention has a sensor chip 10 formed of a semiconductor substrate. The sensor chip 10 has a square shape.

As illustrated in FIG. 12A, the angular points of the square sensor chip 10 are A, B, C, and D, respectively. As illustrated in FIG. 12A, the upper left angle is A, the lower right angle is B, the upper right angle is C, and the lower left angle is D, respectively.

The diagonal line connecting the angles A and B refers to a diagonal line AB. The diagonal line connecting the angles C and D refers to a diagonal line CD. Since the sensor chip 10 has a square shape, the diagonal line AB and the diagonal line CD are orthogonal to each other. Further, the center of the sensor chip 10 refers to a center O.

The center O is matched with an intersection between the diagonal line AB and the diagonal line CD.

As illustrated in FIG. 12B, the sensor chip 10 has a three-layer structure including a first semiconductor layer 1, an insulating layer 2, and a second semiconductor layer 3 serving as a base. For example, a silicon on insulator (SOI) substrate formed of the first semiconductor layer 1, the insulating layer 2 having a thickness of about 0.5 μm, and the second semiconductor layer 3 may be used as the sensor chip 10. The first semiconductor layer 1 and the second semiconductor layer 3 are formed of, for example, n-type single crystal silicon layers. The insulating layer 2 is composed of, for example, a $SiO_2$ layer. The insulating layer 2 is formed on the first semiconductor layer 1. Further, the second semiconductor layer 3 is formed on the insulating layer 2. Accordingly, the insulating layer 2 is disposed between the first semiconductor layer 1 and the second semiconductor layer 3. The insulating layer 2 serves as an etching stopper when etching the first semiconductor layer 1. The second semiconductor layer 3 configures a differential pressure diaphragm 4. As illustrated in FIG. 12B, the differential pressure diaphragm 4 is disposed at the center of the chip.

The differential pressure diaphragm 4 for detecting a differential pressure is provided at the center of the sensor chip 10. As illustrated in FIG. 12B, the first semiconductor layer 1 is removed, thereby forming the differential pressure diaphragm 4. That is, in the differential pressure diaphragm 4, the sensor chip 10 is thin. Herein, as illustrated in FIG. 12A, the differential pressure diaphragm 4 is formed in a square shape. Also, the center of the differential pressure diaphragm 4 and the center O of the sensor chip 10 coincide with each other. That is, the center point of the differential pressure diaphragm 4 is disposed on the intersection of the diagonal line AB and the diagonal line CD. In addition, the differential pressure diaphragm 4 is tilted and disposed at an angle of 45° with respect to the square sensor chip 10. Accordingly, the diagonal line AB passes vertically through the center of two opposite sides of the differential pressure diaphragm 4. Further, the diagonal line CD passes vertically through the center of two different sides of the differential pressure diaphragm 4. The diagonal line of the differential pressure diaphragm 4 has an angle between the diagonal line AB and the diagonal line CD.

Differential pressure gauges 5a to 5d are provided on the surface of the differential pressure diaphragm 4. These four differential pressure gauges 5a to 5d are collectively referred to as a differential pressure gauge 5. The differential pressure gauge 5 is provided at the end of the differential pressure diaphragm 4.

That is, the differential pressure gauge 5 is formed on the peripheral edge portion of the differential pressure diaphragm 4.

The four differential pressure gauges are formed on the side parallel to the diagonal line CD of the differential pressure diaphragm 4. That is, the differential pressure gauge 5 is formed on only two opposite sides of the differential pressure diaphragm 4, and no differential pressure gauge is formed on the other two sides. Herein, the differential pressure gauges 5a and 5c are formed on the side of the angle A, and differential pressure gauges 5b and 5d are formed on the side of the angle B. As described above, two differential pressure gauges 5 are formed on two opposite sides, respectively. Accordingly, the differential pressure gauge 5c is formed in the vicinity of the differential pressure gauge 5a. In addition, the differential pressure gauge 5d is formed in the vicinity of the differential pressure gauge 5b. In other words, the differential pressure gauge 5a is closer to the differential pressure gauge 5c than the differential pressure gauges 5b and 5d and the differential pressure gauge 5b is closer to the differential pressure gauge 5d than the differential pressure gauges 5a and 5c. Therefore, the differential pressure gauges 5a to 5d are not equally spaced in the circumferential direction.

The differential pressure gauge 5a and the differential pressure gauge 5b are opposed to each other with the center O interposed therebetween. The differential pressure gauge 5a and the differential pressure gauge 5b are disposed point-symmetrically with respect to the center O. Also, the differential pressure gauge 5c and the differential pressure gauge 5d are opposed to each other with the center O interposed therebetween. The differential pressure gauge 5c and the differential pressure gauge 5d are disposed point-symmetrically with respect to the center O. The differential pressure gauge 5a and the differential pressure gauge 5d are disposed at positions opposed to each other with the differential pressure diaphragm 4 interposed therebetween. The differential pressure gauge 5b and the differential pressure gauge 5c are disposed at positions opposed to each other with the differential pressure diaphragm 4 interposed therebetween. The longitudinal direction of the differential pressure gauges 5a and 5b is perpendicular to the diagonal line CD. That is, the differential pressure gauges 5a and 5b are formed vertically to one side of the differential pressure diaphragm 4 on which the differential pressure gauges 5a and 5b are formed. On the other hand, the longitudinal direction of the differential pressure gauges 5c and 5d is formed in parallel to the diagonal line CD. That is, the differential pressure gauges 5c and 5d are formed in parallel with one side of the differential pressure diaphragm 4 on which the differential pressure gauges 5c and 5d are formed. Accordingly, a static pressure gauge 15a and a static pressure gauge 15c which are closely disposed are disposed in a direction orthogonal to each other. Also, a static pressure gauge 15b and a static pressure gauge 15d which are closely disposed are disposed in a direction orthogonal to each other.

The differential pressure gauge 5 is a distortion gauge having a piezo resistance effect. Accordingly, when the sensor chip 10 is distorted, the resistances of the differential pressure gauges 5a to 5d are changed. Further, wires (not illustrated) connected with the differential pressure gauges 5a to 5d are formed on the upper surface of the sensor chip. For example, the wires are connected to both ends of each of the differential pressure gauges 5a to 5d. By the wires, the four differential pressure gauges 5 are connected to a bridge circuit. The differential pressure diaphragm 4 is deformed by a pressure difference in a space separated by the differential pressure diaphragm 4. The differential pressure gauge 5 changes the resistance according to the deformation amount of the differential pressure diaphragm 4. By detecting the change in resistance, the pressure may be measured. The differential pressure gauge 5 is formed on the surface of the sensor chip 10 as illustrated in FIGS. 12B and 12C. The wires (not illustrated) are connected to both ends of the differential pressure gauges 5a to 5d in the longitudinal direction. For example, the differential pressure gauges 5a and 5b are formed in parallel to a <110> crystal axis direction at which the piezo resistance coefficient becomes maximum, in a crystal surface direction 100 of the sensor chip 10.

Further, the sensor chip 10 is provided with two static pressure diaphragms 17c and 17d. These two static pressure diaphragms 17c and 17d are collectively referred to as a static pressure diaphragm 17. As illustrated in FIG. 12C, the first semiconductor layer 1 is removed, thereby forming the static pressure diaphragm 17. That is, in the static pressure diaphragm 17, the sensor chip 10 becomes thin. The static pressure diaphragm 17 is disposed on the outer periphery of the differential pressure diaphragm 4. That is, the static pressure diaphragm 17 is disposed outside the differential pressure diaphragm 4. The two static pressure diaphragms 17c and 17d are arranged in point symmetry with respect to the center O.

Accordingly, the static pressure diaphragm 17c and the static pressure diaphragm 17d are disposed to face each other with the differential pressure diaphragm 4 interposed therebetween. The static pressure diaphragm 17c and the static pressure diaphragm 17d are disposed on the diagonal line CD. In addition, a distance to the static pressure diaphragm 17c at the center O and a distance to the static pressure diaphragm 17d at the center O are equal to each other. The static pressure diaphragm 17c and the static pressure diaphragm 17d have the same size and shape. The static pressure diaphragm 17 is smaller than the differential pressure diaphragm 4.

The static pressure diaphragm 17c is disposed between the center O and the angle C. That is, the static pressure diaphragm 17c is disposed between one side of the angle C side of the differential pressure diaphragm 4 and the angle C. Herein, one side of the angle C of the differential pressure diaphragm 4 is a side where the differential pressure gauge 5 is not formed. Also, the static pressure diaphragm 17d is disposed between the center O and the angle D. That is, the static pressure diaphragm 17d is disposed between one side of the angle D side of the differential pressure diaphragm 4 and the angle D. One side of the angle D side of the differential pressure diaphragm 4 is a side where the differential pressure gauge 5 is not formed and a side opposed to one side of the angle C of the differential pressure diaphragm 4.

The static pressure diaphragm 17 is formed in a rectangular shape. Accordingly, the long side and the short side of the static pressure diaphragm 17 are perpendicular to each other. That is, the static pressure diaphragm 17 has a longitudinal direction and a lateral direction. Herein, the direction extending to the outside from the center of the sensor chip 10 refers to a diameter direction (r direction). That is, the direction from the center point of the sensor chip 10 to the end of the sensor chip 10 is a diameter direction. Since the centers of the sensor chip 10 and the differential pressure diaphragm 4 coincide with each other, this diameter direction becomes the diameter direction with respect to the center of the differential pressure diaphragm 4. In addition, a direction orthogonal to the diameter direction is a circumferential direction (θ direction). The circumferential direction corresponds to a tangential direction of a circle based on the center of the sensor chip 10. The short side of the static pressure diaphragm 17 is parallel to the diameter direction.

The short sides of the static pressure diaphragms 17c and 17d are parallel to the diagonal line CD. As described above, the two static pressure diaphragms 17c and 17d opposed to each other are parallel to each other in a width direction. Further, on the diagonal line CD, the longitudinal direction and the circumferential direction of the static pressure diaphragm 17 are parallel to each other. The static pressure diaphragm 17c is provided with the static pressure gauges 15a and 15c. The static pressure diaphragm 17d is provided with the static pressure gauges 15b and 15d.

The static pressure gauges 15a and 15b are formed at the end of the static pressure diaphragm 17. That is, the static pressure gauge 15a overlaps with the peripheral edge of the static pressure diaphragm 17c. The static pressure gauge 15a is formed on the side of the angle C side of the static pressure diaphragm 17c. The static pressure gauge 15a is formed on the long side of the static pressure diaphragm 17c along the long side. The static pressure gauge 15b overlaps with the peripheral edge of the static pressure diaphragm 17d. The static pressure gauge 15b is formed on the side of the angle D side of the static pressure diaphragm 17d. The static pressure gauge 15b is formed on the long side of the static pressure diaphragm 17d along the long side thereof.

The static pressure gauge 15a is opposed to the static pressure gauge 15b with the differential pressure diaphragm 4 interposed therebetween. The static pressure gauge 15a and the static pressure gauge 15b are arranged symmetrically with respect to the center O. The distance from the center O of the sensor chip 10 to the static pressure gauge 15a is equal to the distance from the center O of the sensor chip 10 to the static pressure gauge 15b.

Meanwhile, the static pressure gauges 15c and 15d are formed at the center of the static pressure diaphragm 17. That is, the static pressure gauge 15c is formed inside the peripheral edge of the static pressure diaphragm 17c. The static pressure gauge 15d is formed inside the peripheral edge of the static pressure diaphragm 17d. Accordingly, the static pressure gauges 15c and 15d are disposed between the static pressure gauge 15a and the static pressure gauge 15b. That is, the static pressure gauge 15a, the static pressure gauge 15c, the static pressure gauge 15d, and the static pressure gauge 15b are arranged in sequence in a direction toward the angle D from the angle C. In addition, the differential pressure diaphragm 4 is disposed between the static pressure gauge 15c and the static pressure gauge 15d.

The static pressure gauge 15c is opposed to the static pressure gauge 15d with the differential pressure diaphragm 4 interposed therebetween. The static pressure gauge 15c and the static pressure gauge 15d are arranged symmetrically with respect to the center O. Accordingly, the distance from the center O of the sensor chip 10 to the static pressure gauge 15c is equal to the distance from the center O of the sensor chip 10 to the static pressure gauge 15d. In addition, the distance from the center O to the static pressure gauge 15a is larger than the distance from the center O to the static pressure gauge 15c. The static pressure gauges 15a and 15c are formed on the angle C side from the center O. The static pressure gauges 15b and 15d are formed on the angle D side from the center O.

The static pressure gauges 15a, 15b, 15c and 15d are the same distortion gauges as the differential pressure gauge 5. Accordingly, when the sensor chip 10 is distorted, the resistances of the static pressure gauges 15a, 15b, 15c and 15d are changed by the piezo resistive effect. The static pressure gauges 15a, 15b, 15c and 15d are connected to the bridge circuit in the same manner as the differential pressure gauge 5. As a result, static pressure may be measured. Also, the static pressure gauges 15a, 15b, 15c and 15d are formed on the surface of the sensor chip 10 as illustrated in FIGS. 12B and 12C. Wires (not illustrated) are connected to both ends of the static pressure gauges 15a, 15b, 15c and 15d in the longitudinal direction. In addition, like the differential pressure gauge 5, the static pressure gauges 15a, 15b, 15c and 15d are connected to the bridge circuit.

Herein, the static pressure diaphragms 17c and 17d are formed outside the side on which the differential pressure gauge 5 of the differential pressure diaphragm 4 is not formed. That is, since the differential pressure gauge 5 is formed on the side of the angle A side and the side of the angle B side in the differential pressure diaphragm 4, the static pressure diaphragms 17c and 17d are not formed between the angle A and the differential pressure diaphragm 4 and between the angle B and the differential pressure diaphragm 4. The static pressure diaphragm 17 is disposed at the end of the sensor chip 10 from the different side (a side vertical to the diagonal line CD) from the two sides (sides parallel to the diagonal line CD) of the differential pressure diaphragm 4 with the differential pressure gauge 5.

As a result, the effect on the differential pressure gauge 5 when the static pressure is applied is reduced. The distance between the differential pressure gauge 5 and the static pressure diaphragm 17 may be taken other than the configuration in which the differential pressure gauge 5 is disposed on each side of the differential pressure diaphragm 4. Accordingly, the differential pressure may be measured more accurately. Further, a distance between the static pressure gauge 15 and the differential pressure diaphragm 4 may be taken other than a configuration in which four static pressure diaphragms 17 are provided on the outer circumferential portion of the differential pressure diaphragm 4. Accordingly, the effect on the static pressure gauge 15 when the differential pressure is applied may be reduced. As a result, the static pressure may be measured more accurately.

As such, the static pressure and the differential pressure may be accurately measured. Gaps between the differential pressure diaphragm 4 and the static pressure gauges 15a to 15d may be increased. Therefore, the effect on the stress generated in the adjacent diaphragms may be reduced.

That is, an effect on a crosstalk generated by the interference between the static pressure and the differential pressure may be suppressed.

The direction in which the static pressure diaphragm 17 is provided is different from the direction in which the differential pressure gauge 5 is installed. That is, the differential pressure gauges 5a and 5c are disposed between the center O and the angle A, the differential pressure gauges 5b and 5d are disposed between the center O and the angle B, the static pressure diaphragm 17c is disposed between the center O and the angle C, and the static pressure diaphragm 17d is disposed between the center O and the angle D. In the arrangement in the circumferential direction, the differential pressure gauge 5c, the differential pressure gauge 5a, the static pressure diaphragm 17d, the differential pressure gauge 5d, the differential pressure gauge 5b and the static pressure diaphragm 17c are disposed in sequence. In addition, there is no differential pressure gauge 5 between the static pressure diaphragm 17c and the static pressure diaphragm 17d. In other words, the four differential pressure gauges 5a to 5d are disposed outside the region between the static pressure diaphragm 17c and the static pressure diaphragm 17d. The position of the static pressure diaphragm 17c in the circumferential direction is between the differential pressure gauge 5c and the differential pressure gauge 5b. Also, the position of the static pressure diaphragm 17d in the circumferential direction is between the differential pressure gauge 5a and the differential pressure gauge 5d.

The differential pressure gauge 5a in the diameter direction and the differential pressure gauge 5b in the circumferential direction are formed on one side of the differential pressure diaphragm 4. That is, two differential pressure gauges 5a and 5c formed in the orthogonal direction are formed on the same side of the differential pressure diaphragm 4. Further, two differential pressure gauges 5b and 5d formed in an orthogonal direction are formed at the side facing the side. The differential pressure gauges 5a and 5b are provided along the diameter direction and the differential pressure gauges 5c and 5d are provided along the circumferential direction.

In addition, the bridge circuit is formed by only two opposed sides. Further, the static pressure diaphragm 17 is disposed in a direction in which the differential pressure gauge 5 is not provided. That is, the static pressure diaphragm 17 is formed outside the side where the differential pressure gauge 5 is not provided. In FIG. 12A, the static pressure diaphragm 17 is not formed on the diagonal line AB. By this configuration, it is possible to accurately measure the static pressure and the differential pressure.

That is, a compact and high-performance pressure sensor may be realized. Further, in the embodiment, the differential pressure gauges 5a to 5d are formed on the side of the differential pressure diaphragm 4, but the differential pressure gauges 5a to 5d may be formed at positions where the maximum stress occurs in the vicinity of the ends of the differential pressure diaphragm.

Further, the sensor chip 10 is bonded to a pedestal 11. A region where the pedestal 11 and the sensor chip 10 are bonded to each other is referred to as a bonding region 13A. A region where the pedestal 11 and the sensor chip 10 are not bonded to each other is referred to as a non-bonding region 13. That is, as illustrated in FIG. 12B, a thin wall portion is formed at the end portion of the pedestal 11, and a thick wall portion is formed at the center portion. The thin wall portion is lower than the thick wall portion in height. The thick wall portion is bonded to the sensor chip 10. Meanwhile, at the thin wall portion, the pedestal 11 and the sensor chip 10 are not bonded to each other. Accordingly, the non-bonding region 13 is disposed outside the bonding region 13A.

Herein, the non-bonding region 13 is formed on each of the angle A side and the angle B side. In addition, each of the non-bonding regions 13 has a triangular shape. That is, one of the non-bonding regions 13 has a right-angled triangular shape with the angle A as an apex, and the other non-bonding region 13 has a right-angled triangular shape with the angle B as an apex. The non-bonding regions 13 having the triangular shape are opposed to each other with the bonding region 13A interposed therebetween. That is, two non-bonding regions 13 are formed symmetrically with respect to the diagonal line CD. The bonding region 13A is disposed between two non-bonding regions 13. A through-hole 18 is formed at the center of the bonding region 13A. The through-hole 18 formed in the pedestal 11 is in communication with the differential pressure diaphragm 4. As a result, the through-hole 18 serves as an introduction port and gas may be thus introduced into the differential pressure diaphragm 4.

Further, the bonding region 13A has a hexagonal shape. A boundary line between the bonding region 13A and the non-bonding region 13 is parallel to the diagonal line CD.

As described above, a direction in which the non-bonding region 13 is installed differs from the direction in which the static pressure diaphragm 17 is installed. That is, the non-bonding region 13 is installed in a region between the center O and the angle A and a region between the center O and the angle B and the static pressure diaphragm 17 is installed in a region between the center O and the angle C and a region between the center O and the angle D. In other words, the non-bonding region 13 is not installed on the outside and inside of the static pressure diaphragm 17 in the diagonal line CD direction. The non-bonding region 13 is formed between a side different from two sides on which the differential pressure gauge 5 of the differential pressure diaphragm 4 is formed and the end of the sensor chip 10.

The sizes of the non-bonding region 13 and the bonding region 13A are adjusted so that the stress generated in the direction of the diagonal line AB and the stress generated in the direction of the diagonal line CD vertical thereto are equal to each other. By such a configuration, a temperature characteristic may be enhanced.

That is, as illustrated in Japanese Patent No. 3359493, a zero shift due to temperature and the fluctuation thereof are minimized to obtain a favorable temperature characteristic. Further, the static pressure diaphragm 17 may not be disposed in the vicinity of the non-bonding region 13. Therefore, a space for forming the non-bonding region 13 may be ensured. As a result, a compact and high-performance pressure sensor may be realized.

Pressure Sensor—Second Embodiment

Figure 13A:
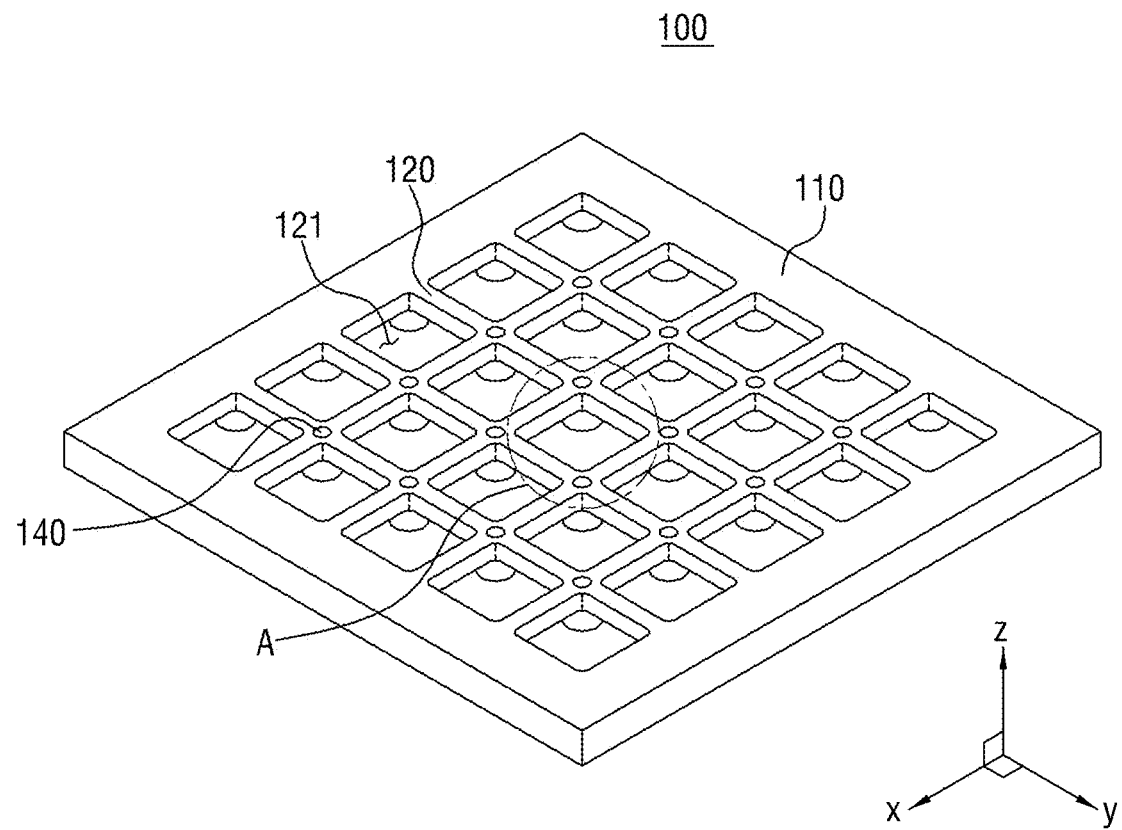
Figure 13B:
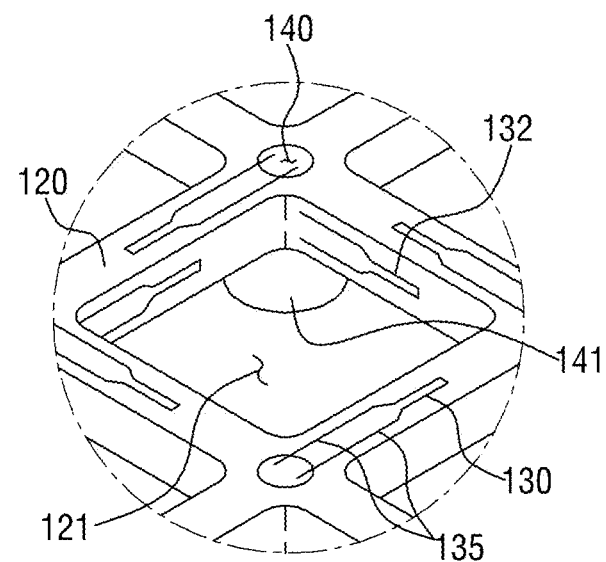

FIGS. 13A to 13C illustrate another embodiment of a pressure sensor according to the present invention.

It is assumed that the reference numerals illustrated in FIGS. 13A to 13C are independent from other drawings.

Referring to FIGS. 13A to 13C, a deformation measuring sensor 100 of the first embodiment includes a frame 110, a plurality of beams 120, strain gauges 130, 131 and 132, and a wire groove 140.

The frame 110 has a hollow space at the center and has a shape covering the plurality of beams 120, and has a thickness which is relatively larger than that of the plurality of beams 120.

The plurality of beams 120 are formed in a lattice shape with a space 121 opened in a penetrated shape of the frame 110 as a deformation structure depending on pressure or shear force. The plurality of beams 120 is relatively thinner than the frame 110, and thus, it is easy to deform due to pressure or shear force.

Each of the strain gauges 130, 131 and 132 is attached to the upper or lower surface of each beam 120 and attached to at least one of both sides of the beam 120 to measure the strain.

The strain gauge 130 attached to the upper surface of the beam 120 and the strain gauge 131 attached to the lower surface of the beam 120 measure the strain of the beam 120 depending on the pressure. That is, when the pressure is applied in a Z-axis direction which is vertical to the beam 120, the beam 120 is deformed, and the strain gauges 130 and 131 measure the strain.

The strain gauge 132 attached to the side of the beam 120 measures the strain of the beam 120 depending on the shear force. That is, when the shear force is applied in an X-axis or Y-axis direction which is horizontal to the beam 120, the beam 120 is deformed, and the strain gauge 132 measures the strain.

The wire groove 140 is a configuration for the wire 135 of the strain gauges 130, 131 and 132 and the wire 135 is connected to a lead for signal processing or the like through the wire groove 140.

At this time, the wire groove 140 is located at the intersection of the plurality of beams 120 so as to allow the wire 135 of each of the strain gauges 130, 131, 132 to pass therethrough.

In addition, the wire groove 140 is formed by passing through the intersection of the plurality of beams 120 and a support 141 formed below the corresponding intersection.

In this case, the sum of the thickness of the intersection of the plurality of beams 120 and the thickness of the support 141 is equal to the thickness of the frame 110.

In this configuration, the support 141 serves to support the intersection portion of the plurality of beams 120 when the deformation measuring sensor 100 is mounted on the substrate. Accordingly, when the deformation measuring sensor 100 is mounted on the substrate, the beam 120 may be easily deformed according to the pressure or shear force.

In addition, the support 141 serves to reduce the deformation of the other beam 120 due to the interference received when the pressure or shear force is applied to the specific beam 120.

Since both ends of the beam 120 are connected to the intersection of the plurality of beams 120 or the frame 110 in the deformation measurement sensor 100, the strain depending on the pressure is largest at the center of the single beam 120. Accordingly, it is preferred that the measurement center of the strain gauges 130, 131, and 132 is located at the center of each beam 120.

In the deformation measuring sensor 100, the beam 120 has various shapes, such as a prism, a cylinder, a pyramid with cut ends, a column having a thinner thickness than the other portion at both ends, a column having a larger thickness than the other portion at both ends, and a column having at least one gradient shape in a longitudinal direction, which are easy to measure the strain depending on the pressure or shear force.

The shape of the plurality of beams 120 in the deformation measuring sensor 100 of the first embodiment is formed in a lattice shape with the space 121 interposed therebetween and has a structure in which both ends are connected to the intersection of the plurality of beams 120 or the frame 110. As a result, the strain depending on the pressure or shear force becomes relatively larger as compared with the case where the strain gauge is attached to a normal planar substrate to measure the strain.

Further, in the deformation measuring sensor 100, even though the deformation structure deformed depending on the pressure and the deformation structure deformed depending on shear force are not separately provided, the strain depending on the pressure or shear force can be measured in the lattice-shaped beam 120 which is the same deformation structure.

Accordingly, in the deformation measuring sensor 100, the beam 120, which is the deformation structure depending on the pressure or shear force, can be manufactured in a small size, thereby reducing the overall size of the deformation measuring sensor 100.

Like the related art, when the strain gauge is located on a planar substrate to measure the strain depending on pressure, the strain depending on pressure is not large as a whole, and thus, measurement accuracy is deteriorated. In addition, since the strain is relatively small at the edge of the substrate and the strain is relatively large at the center of the substrate, it is difficult to measure the pressure at the multi-points because it is advantageous to measure the strain when the strain gauge is located at the center of the substrate.

On the other hand, in the deformation measuring sensor 100, the beam 120, which is the lattice-shaped deformation structure, is provided to measure the strain depending on pressure applied to the multiple points and simultaneously measure the strain depending on shear force at the multiple points.

In the deformation measuring sensor 100, the frame 110 or the beam 120 may be made of a material such as steel, nickel-chrome-molybdenum steel, stainless steel, tool steel, hardened stainless steel, aluminum alloys or duralumin, and it is possible to adopt various materials depending on the material property of each material.

Pressure Sensor—Third Embodiment

FIGS. 14A to 14D illustrate another embodiment of the pressure sensor according to the present invention.

It is assumed that the reference numerals in the drawings illustrated in FIGS. 14A to 14D are independent of those of other drawings.

The embodiments discussed in the present specification provide an absolute pressure sensor that provides improved performance in a small die size. One embodiment provides an active electrode of a pressure measurement capacitor Cp.

One embodiment provides a reference capacitor Cref that varies slightly or does not change at all with pressure. One embodiment provides an electrical connection unit that is not almost present or may not be present with a pressure port opening for the capacitor Cp and the reference capacitor Cref on a single wafer. In one embodiment, the sensor is compatible with all media.

In one embodiment, a silicon die, or a wafer or a wafer assembly includes a vibratory diaphragm 124, and the silicon die has a silicon die top 128 at an opposite side to a silicon die bottom 126, a top silicon die port 124 extends from the silicon die top to the top of the vibratory diaphragm through the silicon die, and a bottom silicon die port 110 extends from the silicon die bottom to the bottom of the vibratory diaphragm. In one embodiment, the bottom silicon die port 110 has a larger cross-sectional area than the top silicon die port 124. In one embodiment, a capacitor electrode 116 is positioned to pass through the bottom silicon die port 110 along the bottom of the silicon die 126. In one embodiment, the capacitor electrode 116 includes a first signal generating unit 142. In one embodiment, the first signal generating unit 142 spans the same space as the top silicon die port 124. In one embodiment, the capacitor electrode includes a second signal generating unit 114. In one embodiment, the second signal generating unit 114 surrounds the first signal generating unit 142. In one embodiment, the top silicon die port 124 has a circular cross-section. In one embodiment, the bottom silicon die port 110 has the circular cross-section.

In one embodiment, the capacitor electrode 116 is a layer that defines a cavity that includes the bottom silicon die port 110. In one embodiment, the cavity is configured to be sealed under vacuum relative to an atmosphere in which the vibratory diaphragm is exposed. In one embodiment, the seal is hermetic.

In one embodiment, the die 100 includes a bottom portion 144 including the vibratory diaphragm and a top portion 146 connected to the bottom portion. In one embodiment, the top portion 146 of the silicon die is connected to the bottom portion 144 of the silicon die in a layer 104 containing silicon dioxide.

In one embodiment, differential measurement from the cavity 110 enables erasure of one or more common mode errors such as temperature, pressure leakage, electronic device charge injection, and the like. In one embodiment, under applied pressure, the diaphragm is deflected to change Cp. In one embodiment, a region over Cref is thicker than the diaphragm and is less deflected under applied pressure. In one embodiment, the diaphragm deflection is proportional to the cube of the diaphragm thickness, and as a result, it is easy to achieve little deflection for Cref. In one embodiment, for barometric pressure measurement, a 13-µm thickness diaphragm having a diameter of 300 µm is used with a 460-µm diameter Cref along the circumference of Cp. In one embodiment, a gap of 10 µm extends between Cref and Cp around Cref and Cp as if surrounding Cref and Cp. In the embodiment with the parameters, pressure sensitivity of Cref is approximately one thousandth of the pressure sensitivity of Cp, thereby providing a reference electrode that works excellently. In one embodiment, for the dimensions described above, the Cp electrode has a capacitance of 0.09 mm$^2$. In one embodiment, with a 1 µm gap 122, Cp will correspond to 0.8 pF. In one embodiment, the noise density of a high-performance low-power electronic device is approximately 10 zF/$\sqrt{Hz}$, which results in a resolution of 1/80,000,000 for a 1 Hz bandwidth. In one embodiment, this provides 26-bit resolution. In one embodiment, the resolution for an atmospheric pressure range includes the same full scale as approximately 50% of Cp. In one embodiment, the capacitor configured as such has a resolution of approximately 0.2 cm (altitude).

In one embodiment, the capacitor electrode layer 116 is formed of metal such as AlGe, AuSn, Cu, or the like. In one embodiment, the capacitor electrode layer 116 may be used to bond the wafer 100 to the substrate 112 to create a reference vacuum cavity 110.

In one embodiment, the bonding is hermetic bonding. In one embodiment, the same metal may be used to form one or both of the Cp 116 and Cref 114 electrodes.

In one embodiment, a metal temperature coefficient of such an electrode is approximately 10 to 20 ppm/° C. In one embodiment, when the temperature is changed, the gap 120 disposed between Cp and Cref is changed to a temperature variation, which may cause a temperature error. The subject matter of the present invention provides several advantages to overcome this error. In one embodiment, first level of temperature common mode rejection is achieved by bringing bond metal and electrode metal to a similar thickness.

In one embodiment, second level of temperature common mode rejection is achieved by forming the Cp electrode and the Cref electrode of the same material or a continuous material.

In one embodiment, a silicon fusion bond is used to create a bond 108 for bonding the capacitor electrode layer including the active electrode to other parts of the sensor, Cp, and Cref. As a result, in some embodiments, Cp and Cref are formed by any of a number of processes including diffusion, ion implantation, polysilicon and/or thin film deposition and such processes are not limited to those listed above. In one embodiment, for the capacitor electrode formed as such, the first level of temperature common mode rejection is not required, as the fusion bond provides monocrystalline silicon.

The second level common mode rejection is similar to the common mode rejection.

In one embodiment, the sensor may be manufactured using at least one of three masks, a pressure sensor cavity, a gap cavity, and an electrode pattern.

Figure 14B:
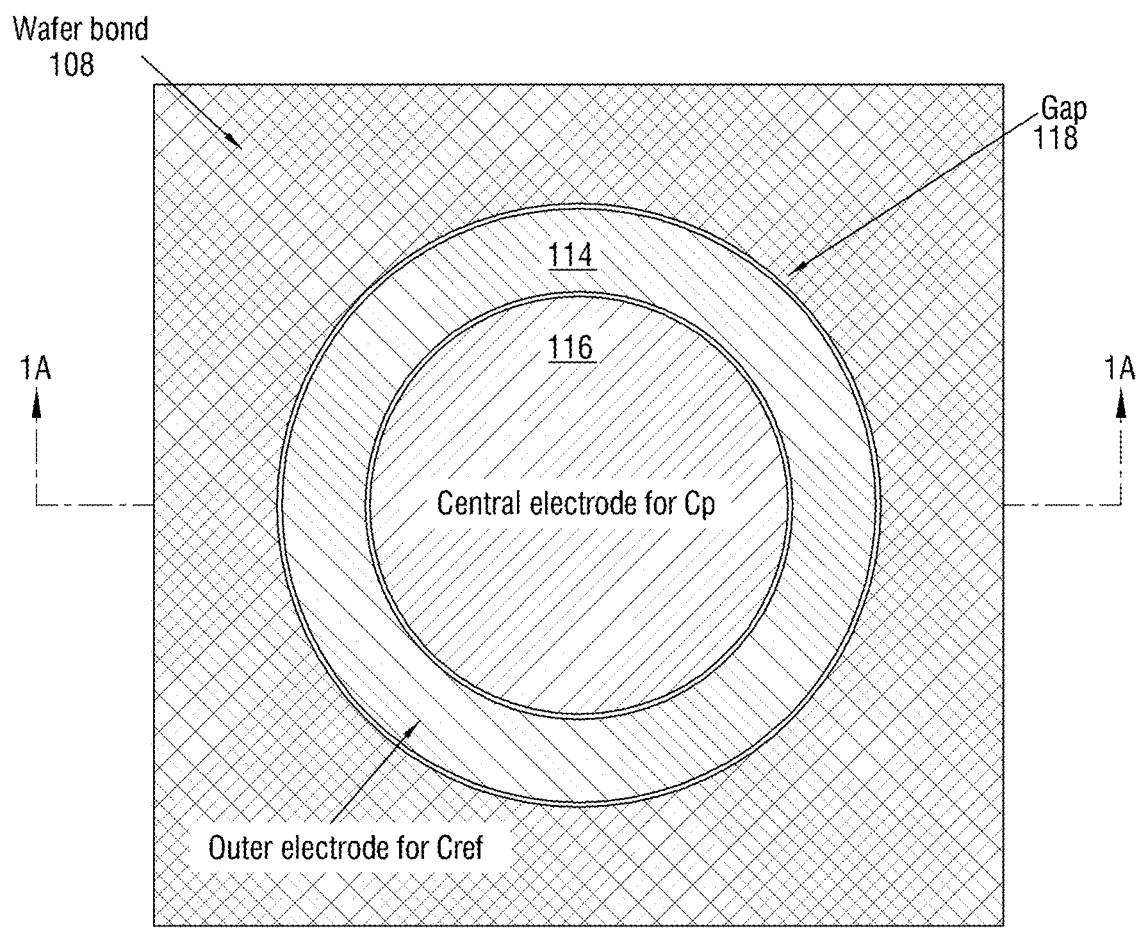
Figure 14C:
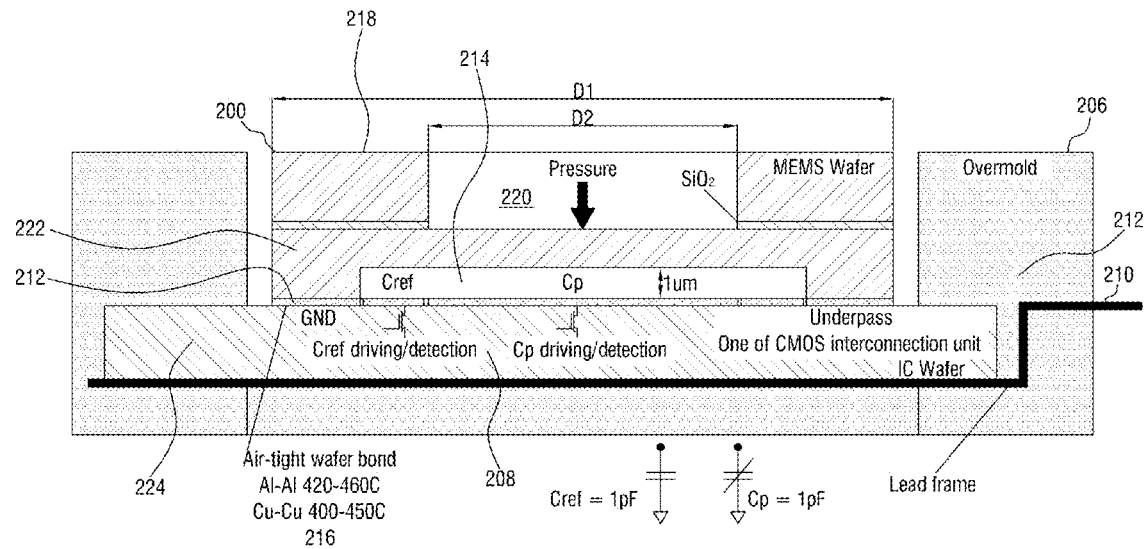

FIG. 14C illustrates an active electrode bonded to a wafer to form a vertically integrated pressure sensor according to one embodiment. In one embodiment, the wafer or substrate 112 includes an application specific integrated circuit (ASIC) 120. In one embodiment, the active electrode 212 is bonded to the ASIC wafer. In one embodiment, the active electronic device is directly connected to the metal electrode. In one embodiment, the connection may reduce shunt capacitance. In one embodiment, an electrical signal from a vacuum cavity is achieved through diffused underpass.

In one embodiment, cost-effective packaging of the sensor 200 is achieved by overmolding the sensor, such as by using plastic overmolding. In one embodiment, the overmolding 206 defines a hole through which the integrated sensor 200 is positioned on the leadframe 210. In one embodiment, the substrate such as the ASIC is overmolded with plastic.

In one embodiment, the sensor 200 does not contact an overmold 206, for example, to prevent induced stress that may affect performance.

In one embodiment, a top portion 218 of the die is circular. In one embodiment, the top portion of the die has a diameter D1 of approximately 600 µm.

In one embodiment, a top port 220 of the die is circular. In one embodiment, the top port of the die has a diameter D2 of approximately 600 µm. In one embodiment, an ASIC 224 includes electronic devices including a drive electronic device for Cp, a drive electronic device for Cref, a sense electronic device for Cp, and a sense electronic device for Cref, but is not limited to.

In one embodiment, a bottom portion 222 of the die is connected with the ASIC 224. In one embodiment, the bond includes aluminum to aluminum bond. In one embodiment, the bond is formed at approximately 420° C. to approximately 460° C.

In one embodiment, the bond includes copper to copper bond. In one embodiment, the bond is formed at approximately 400° C. to approximately 450° C. In one embodiment, the bottom portion 222 of the die is grounded to the ASIC 224. In one embodiment, the capacitance of Cref is approximately 1 pF, and the capacitance remains substantially constant in use. In one embodiment, the capacitance of Cp is approximately 1 pF, and the capacitance is changed in use.

One embodiment includes wire bond 212. In one embodiment, the wire bond 212 is connected to an underpass positioned in the ASIC 224. In one embodiment, the underpass includes at least one complementary metal oxide semiconductor (CMOS) interconnect.

Figure 14D:
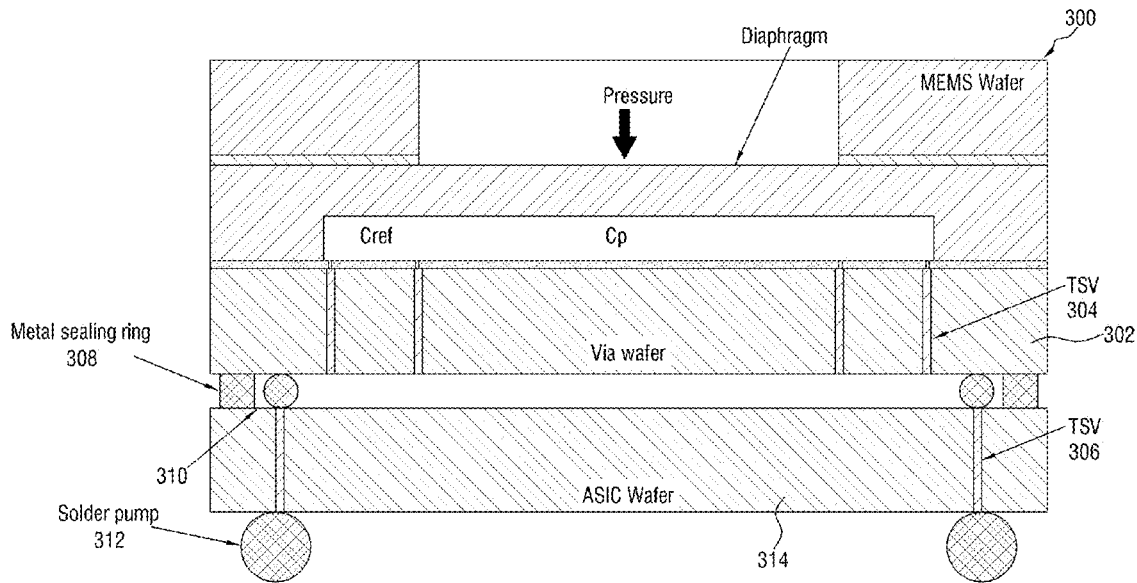

FIG. 14D is a diagram illustrating a chip-scale packaged pressure sensor using a through-silicon-via wafer as a substrate and a solder bump for connecting the sensor to an integrated circuit wafer and connecting the integrated circuit wafer to a printed circuit board according to one embodiment. In one embodiment, a substrate 302 is a low resistivity through silicon via (TSV) wafer. In one embodiment, the TSV 304 is selected to reduce the shunt capacitance, which patent application is incorporated herein by reference in its entirety. In one embodiment, one or both of the capacitor electrodes Cp and Cref are formed by a trench. In one embodiment, the solder bump is used to connect the via wafer 302 to another substrate such as an ASIC wafer 306. In one embodiment, solder bumps 310 and 312 are used to connect the substrate 306 to another substrate such as a PCB.

In one embodiment, a sensor 300 is bonded to the ASIC wafer 306 through a seal ring such as a metal seal ring 308. In one embodiment, the seal ring 308 is made of metal. In one embodiment, the seal ring 308 provides a moisture seal.

In one embodiment, the ASIC wafer includes one or more TSVs 306 to provide connectivity to another substrate such as the PCB across the wafer.

The method proposed by the present invention based on the aforementioned MRI apparatus, the PET apparatus, the CT apparatus, the thermoplastic mask, and the pressure sensor will be described below in detail.

A system for monitoring a thermoplastic mask proposed by the present invention may include: a mask having a shape determined according to a shape of a first region which is at least a part of a patient's body by using thermoplasticity and fixing the first region in close contact with the first region; an apparatus (MRI apparatus) outputting radiation to the first region fixed by the mask; a pressure sensor provided between the mask and the first region and sensing pressure induced by a space generated between the mask and the first region; and a communication unit transmitting information on the pressure sensed by the pressure sensor to the outside.

The thermoplastic mask, the MRI apparatus, and the pressure sensor have been specifically described above with reference to the drawings.

Further, the contents of the wireless communication unit in FIG. 18 to be described later may be just applied to the communication unit.

Hereinafter, a specific method proposed by the present invention will be described with reference to FIGS. 15 to 17, assuming that the system for monitoring the mask includes the thermoplastic mask, the MRI apparatus, the pressure sensor, and the communication unit.

Figure 15:
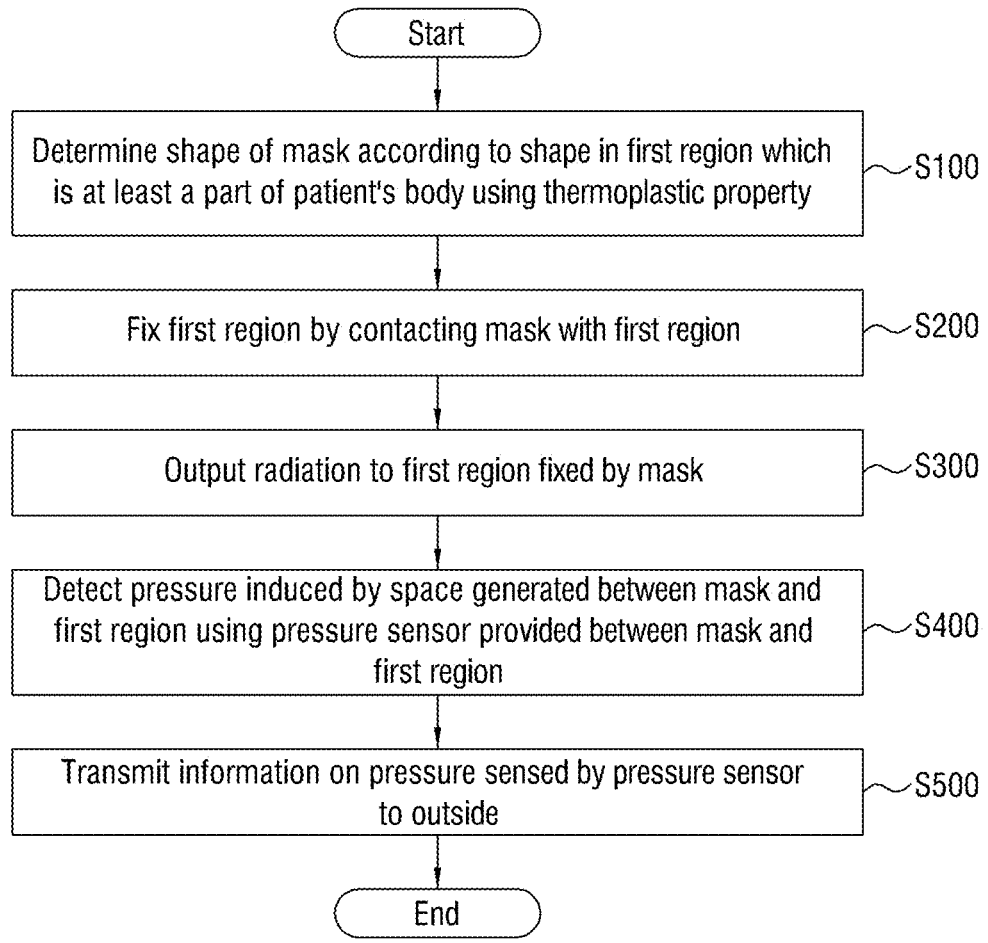
FIG. 15 illustrates an embodiment in which the movement of the head within the mask is determined through the pressure sensor to support safe radiation therapy of the patient.

FIG. 15 illustrates an embodiment in which the movement of the head within the mask is determined through the pressure sensor to support safe radiation therapy of the patient, according to the present invention.

Referring to FIG. 15, in a method of monitoring the thermoplastic mask, step S100 in which the shape of the mask is determined according to the shape of the first region which is at least a part of the patient's body may be preliminarily performed.

Thereafter, step S200 in which the mask fixes the first region in close contact with the first region is performed and step S300 of outputting radiation to the first region fixed by the mask is performed.

In this case, step S400 of sensing pressure induced by a space generated between the mask and the first region by using a pressure sensor provided between the mask and the first region is performed.

In response thereto, step S500 of transmitting information on the pressure sensed by the pressure sensor to the outside is performed.

Accordingly, a system for assisting confirming the movement of a head within a thermoplastic mask by using a pressure sensor and controlling the movement of the head may be provided to the user, in therapy of head and neck cancer.

In particular, in the present invention, the pressure is positioned between the mask and the head and a signal of the pressure sensor is represented by a computer programmed system to confirm whether the movement occurs in the mask and support safe radiation therapy of a patient.

As another embodiment, a step of determining whether the first region is fixed through the mask by using a change in the sensed pressure may be further added.

Figure 16:
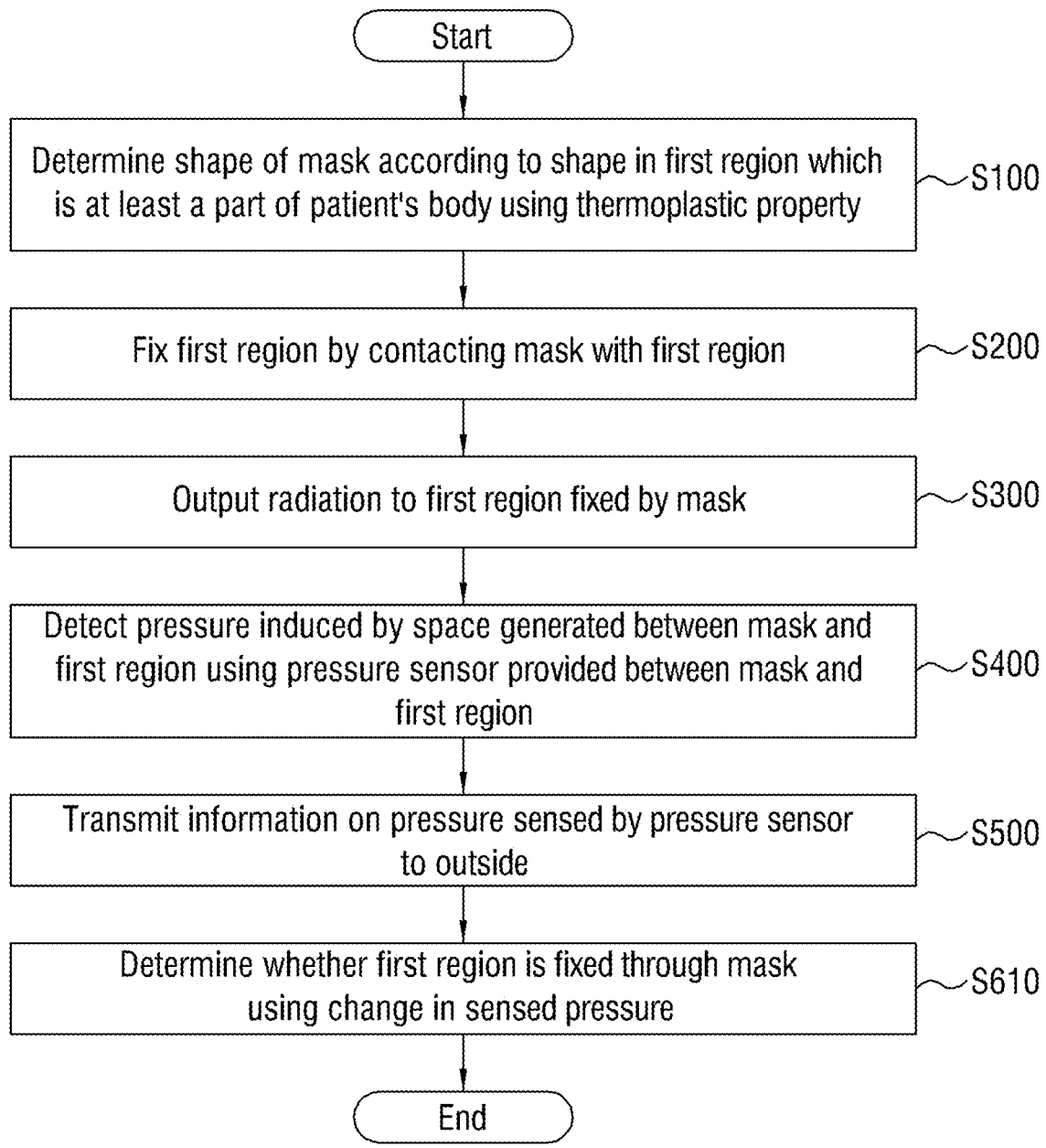
FIG. 16 illustrates another embodiment in which the movement of the head within the mask is determined through the pressure sensor to support safe radiation therapy of the patient.

FIG. 16 illustrates another embodiment in which the movement of the head within the mask is determined through the pressure sensor to support safe radiation therapy of the patient, according to the present invention.

Referring to FIG. 16, steps S100 to S500 are similar to those of FIG. 15, but the method further includes step S610 of determining whether the first region is fixed through the mask by using the sensed pressure change.

Therefore, since it is possible to determine whether the patient and the mask are in close contact with each other in real time at the outside through step S610, it is possible to support effective patient therapy.

Further, as yet another embodiment to which the present invention is applied, a step in which the apparatus stops an output operation of the radiation when the sensed pressure is more than a predetermined numerical value may be further added.

Figure 17:
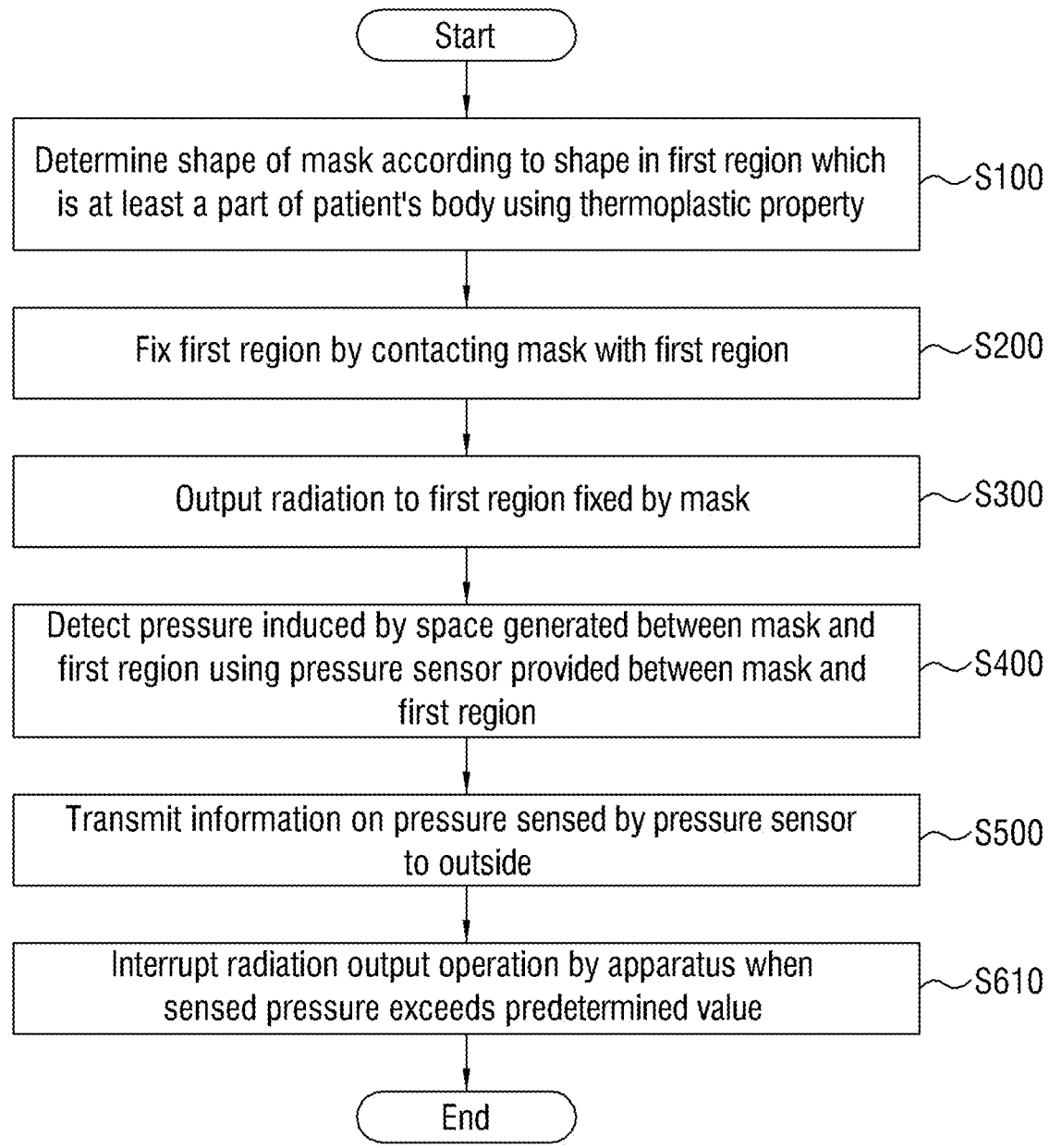
FIG. 17 illustrates yet another embodiment in which the movement of the head within the mask is determined through the pressure sensor to support safe radiation therapy of the patient.

FIG. 17 illustrates yet another embodiment in which the movement of the head within the mask is determined through the pressure sensor to support safe radiation therapy of the patient, according to the present invention.

Referring to FIG. 17, steps S100 to S500 are similar to those of FIG. 15, but the method further includes step S620 of stopping, by the apparatus, the output operation of the radiation when the sensed pressure is more than the predetermined numerical value.

Accordingly, it is determined that the patient and the mask are not in close contact with each other in real time through step S610 at the outside and the radiation therapy is stopped, thereby clearly solving a problem that the patient's health deteriorates unnecessarily due to the therapy.

Figure 18:
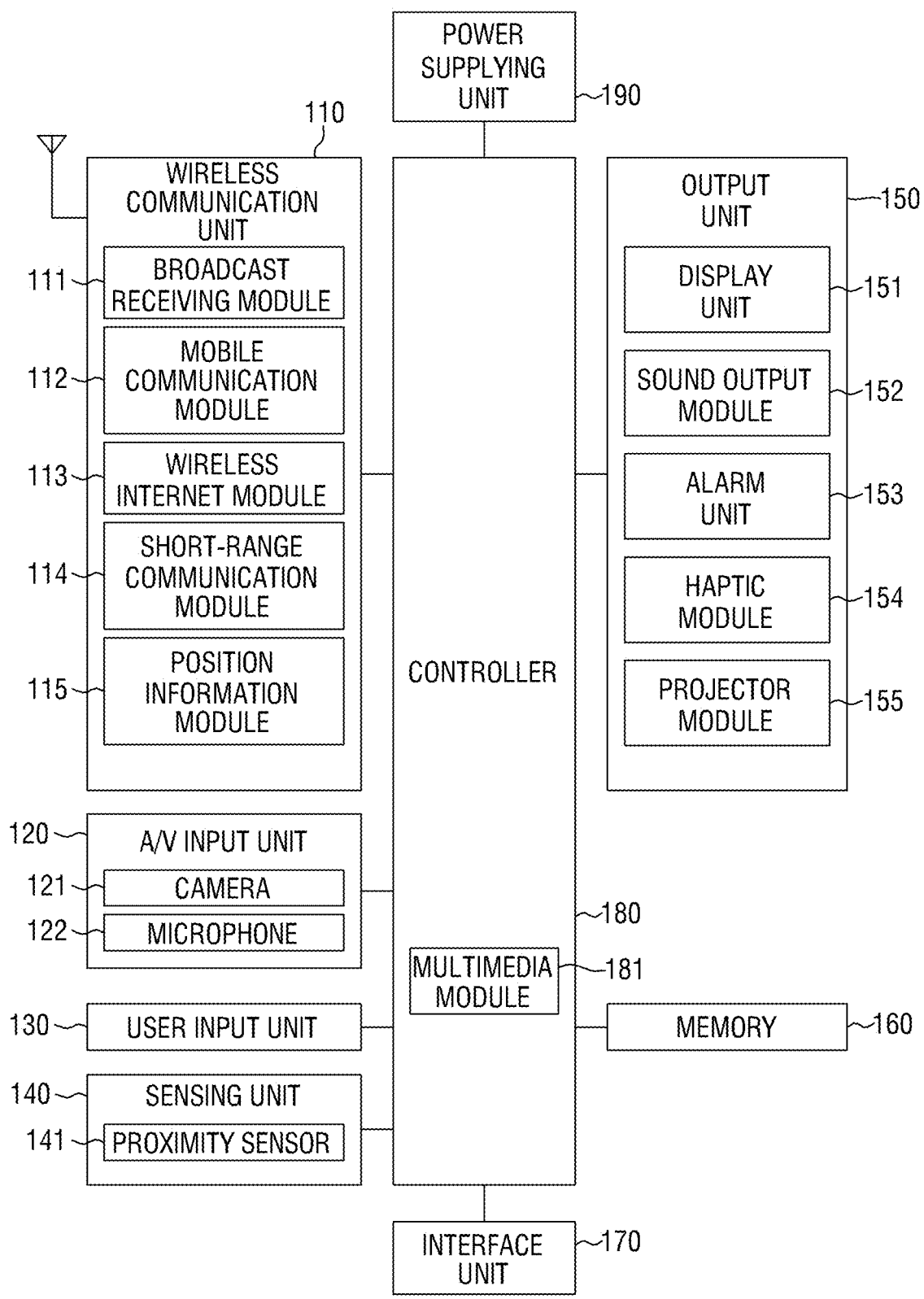
FIG. 18 is a diagram illustrating one example of an apparatus outputting radiation or an external apparatus receiving information on pressure sensed by a pressure sensor.

Meanwhile, FIG. 18 is a diagram illustrating one example of an apparatus outputting radiation or an external apparatus receiving information on pressure sensed by a pressure sensor, which are applied to the present invention.

It is assumed that reference numerals used in FIG. 18 are independent from the reference numerals used in the drawings.

The apparatus outputting the radiation or the external apparatus receiving information may include a wireless communication unit 110, an audio/video (A/V) input unit 120, a user input unit 130, a sensing unit 140, an output unit 150, a memory 160, an interface unit 170, a controller 180, and a power supply unit 190.

The components illustrated in FIG. 18 are not required. Therefore, the apparatus outputting the radiation or the external apparatus receiving the information, having more components therethan or less components therethan, may be implemented.

Hereinafter, the components will be described in sequence.

The wireless communication unit 110 may include one or more modules which enable wireless communication between the apparatus outputting the radiation or the external apparatus receiving the information and a wireless communication system or the apparatus outputting the radiation or the external apparatus receiving the information and a network in which the apparatus outputting the radiation or the external apparatus receiving the information is positioned. For example, the wireless communication unit 110 may include a broadcast receiving module 111, a mobile communication module 112, a wireless Internet module 113, a short-range communication module 114, and a positional information module 115.

The broadcast receiving module 111 receives broadcast signals and/or broadcast-related information from an external broadcast management server through a broadcast channel.

The broadcast channel may include a satellite channel and a terrestrial channel. The broadcast management server may be a server for generating and transmitting the broadcast signals and/or broadcast related information or a server for receiving previously generated broadcast signals and/or broadcast related information and transmitting the received broadcast signals and/or broadcast related information to the apparatus. The broadcast signals may include a TV broadcast signal, a radio broadcast signal, and a data broadcast signal and include even a broadcast signal of a type in which the data broadcast signal is combined with the TV broadcast signal or the radio broadcast signal.

The broadcast-related information may mean information related to the broadcast channel, a broadcast program, or a broadcast service provider. The broadcast-related information may be provided even through a mobile communication network. In this case, the broadcast-related information may be received by the mobile communication module 112.

The broadcast-related information may exist in various types. For example, the broadcast-related information may exist as a type such as electronic program guide (EPG) of digital multimedia broadcasting (DMB) or electronic service guide (ESG) of digital video broadcast-handheld (DVB-H).

For example, the broadcast receiving module 111 may receive a digital broadcast signal by using a digital broadcast system such as digital multimedia broadcasting-terrestrial (DMB-T), digital multimedia broadcasting-satellite (DMB-S), media forward link only (MediaFLO), digital video broadcast-handheld (DVB-H), and integrated services digital broadcast-terrestrial (ISDB-T). Of course, the broadcast receiving module 111 may be configured to be suitable for other broadcast systems as well as the digital broadcasting system.

The broadcast signal and/or broadcast related information received through the broadcast receiving module 111 may be stored in the memory 160.

The mobile communication module 112 transmits/receives wireless signal with at least one of a base station, an external terminal, and a server on a mobile communication network. The wireless signal may include various types of data depending on transmitting/receiving a voice call signal, a video phone call signal, or a text/multimedia message.

The wireless Internet module 113 which represents a module for wireless Internet access may be internally or externally mounted on the apparatus outputting the radiation or the external apparatus receiving the information. As the wireless Internet technology, wireless LAN (WLAN) (Wi-Fi), wireless broadband (Wibro), world interoperability for microwave access (Wimax), high speed downlink packet access (HSDPA), or the like, may be used.

The short-range communication module 114 represents a module for short-range communication. As short-range communication technology, Bluetooth, radio frequency identification (RFID), infrared data association (IrDA), ultra wideband (UWB), ZigBee, or the like may be used.

Herein, various multiple access schemes may be used, which include code division multiple access (CDMA), frequency division multiple access (FDMA), time division multiple access (TDMA), orthogonal frequency division multiple access (OFDMA), single carrier frequency division multiple access (SC-FDMA), and the like. The CDMA may be implemented as radio technology such as universal terrestrial radio access (UTRA) or CDMA2000. The TDMA may be implemented as radio technology such as global system for mobile communications (GSM)/general packet radio service (GPRS)/enhanced data rates for GSM evolution (EDGE). The OFDMA may be implemented as radio technology such as Institute of Electrical and Electronics Engineers (IEEE) 802.11 (Wi-Fi), IEEE 802.16 (WiMAX), IEEE 802.20, Evolved UTRA (E-UTRA), or the like. The UTRA is part of Universal Mobile Telecommunications System (UMTS). 3rd Generation Partnership Project (3GPP) Long Term Evolution (LTE) as a part of Evolved UMTS (E-UMTS) using the E-UTRA adopts OFDMA in downlink and adopts SC-FDMA in uplink. LTE-A (Advanced) is evolution of LTE. IEEE 802.16m is evolution of IEEE 802.16e.

The position information module 115 is a module for acquiring the position of the apparatus outputting the radiation or the external apparatus receiving the information and a representative example thereof is a global position system (GPS) module.

Referring to FIG. 18, an audio/video (A/V) input unit 120 which is used for inputting an audio signal or a video signal may include a camera 121 and a microphone 122. The camera 121 processes an image frame such as a still image or a moving picture obtained by an image sensor in a video communication mode or a photographing mode. The processed image frame may be displayed on the display unit 151.

The images frame processed by the camera 121 may be stored in the memory 160 or transmitted to the outside through the wireless connection unit 110. Two or more cameras 121 may be provided according to a use environment.

The microphone 122 receives an external sound signal by a microphone in a recording mode, a voice recognition mode, or the like, and processes the received external sound signal as electrical voice data. The processed voice data may be converted into a transmittable form and transmitted to a mobile communication base station through the mobile communication module 112. Various noise removal algorithms may be implemented in the microphone 122 to remove noise generated in receiving the external sound signal.

The user input unit 130 generates input data for the user to control the operation of the apparatus. The user input unit 130 may include a keypad, a dome switch, a touch pad (resistive/capacitive), a jog wheel, a jog switch, and the like.

The sensing unit 140 generates a sensing signal for controlling the operation of the apparatus outputting the radiation or the external apparatus receiving the information by sensing a current state of the apparatus outputting the radiation or the external apparatus receiving the information, such as an opening/closing state of the apparatus outputting the radiation or the external apparatus receiving the information, the position of the apparatus outputting the radiation or the external apparatus receiving the information, contact of the user or not, an orientation of the apparatus outputting the radiation or the external apparatus receiving the information, acceleration/deceleration of the apparatus outputting the radiation or the external apparatus receiving the information, or the like.

Further, the sensing unit 140 may sense whether the power supply unit 190 supplies power, whether the interface unit 170 is combined with the external apparatus, and the like. Meanwhile, the sensing unit 140 may include a proximity sensor 141.

The output unit 150 which is used for generating an output related with sight, hearing, or touch may include a display unit 151, a sound output module 152, an alarm unit 153, a haptic module, and a projector module 155.

The display unit 151 displays (outputs) information processed in the apparatus outputting the radiation or the external apparatus receiving the information.

The display unit 151 may include at least one of a liquid crystal display (LCD), a thin film transistor-liquid crystal display (TFT LCD), an organic light-emitting diode (OLED), a flexible display, and a 3D display.

Some of the displays may be configured as a transparent or light transmissive type to view the outside through the displays. This may be called a transparent display and a representative example of the transparent display includes a transparent OLED (TOLED), and the like. A rear structure of the display unit 151 may also be configured as a light transmission structure. By such a structure, the user may see an object positioned behind an apparatus body through a region occupied by the display unit 151 of the apparatus body.

There may be two or more display units 151 according to an implementation form of the apparatus outputting the radiation or the external apparatus receiving the information. For example, in the apparatus outputting the radiation or the external apparatus receiving the information, the plurality of display units may be separated from each other or integrally disposed on one surface, and further, disposed on different surfaces, respectively.

When the display unit 151 and a sensor (hereinafter, referred to as 'touch sensor') sensing a touch motion form a mutual layer structure (hereinafter, referred to as 'touch screen'), the display unit 151 may be used as an input apparatus as well as the output apparatus. The touch sensor may take the form of, for example, a touch film, a touch sheet, a touch pad, or the like.

The touch sensor may be configured to convert a change in pressure applied to a specific portion of the display unit 151 or capacitance generated at the specific portion of the display unit 151 into an electrical input signal. The touch sensor may be configured to detect touch pressure as well as a touched position and area.

When there is a touch input for the touch sensor, a signal(s) corresponding to the touch input is (are) sent to a touch controller. The touch controller processes the signal(s) and thereafter, transmits data corresponding thereto to the controller 180. As a result, the controller 180 may know which region of the display unit 151 is touched.

The proximity sensor 141 may be disposed within an internal region of the apparatus outputting the radiation or the external apparatus receiving the information covered by the touch screen or in the vicinity of the touch screen. The proximity sensor refers to a sensor that detects the presence or absence of an object approaching a predetermined detection surface or an object which exists nearby without mechanical contact using electromagnetic field force or infrared rays. The proximity sensor has a longer lifetime and higher utilization than the touch sensor.

Examples of the proximity sensor include a transmission type photoelectric sensor, a direct reflection type photoelectric sensor, a mirror reflection type photoelectric sensor, a high frequency oscillation type proximity sensor, a capacitive proximity sensor, a magnetic proximity sensor, an infrared proximity sensor, and the like. When the touch screen is a capacitive sensor, the touch screen is configured to detect the proximity of the pointer by a change of an electric field depending on the proximity of the pointer. In this case, the touch screen (touch sensor) may be classified as the proximity sensor.

Hereinafter, for easy description, the act of recognizing that the pointer is positioned on the touch screen while the pointer is not in contact with the touch screen is referred to as "proximity touch" and the act of actually touching the pointer on the screen is referred to as "contact touch". The position where the pointer is proximately touched on the touch screen means a position where the pointer is vertically corresponding to the touch screen when the pointer is touched.

The proximity sensor detects the proximity touch and a proximity touch pattern (e.g., a proximity touch distance, a proximity touch direction, a proximity touch speed, a proximity touch time, a proximity touch position, a proximity touch movement state, and the like). Information corresponding to the sensed proximity touch operation and the proximity touch pattern may be output on the touch screen.

The sound output module 152 may output audio data received from the wireless communication unit 110 or stored in the memory 180 in call signal receiving, a recording mode, a voice recognition mode, a broadcast receiving mode, and the like. The sound output module 152 may also output a sound signal related with a function (e.g., a call signal receiving sound, a message receiving sound, or the like) performed by the apparatus outputting the radiation or the external apparatus receiving the information. The sound output module 152 may include a receiver, a speaker, a buzzer, and the like.

The alarm unit 153 outputs a signal for notifying the occurrence of an event of the apparatus outputting the radiation or the external apparatus receiving the information. Examples of the event which occurs in the apparatus outputting the radiation or the external apparatus receiving the information include call signal reception, message reception, key signal input, touch input, and the like. The alarm unit 153 may also output another form other than a video signal or an audio signal, for example, a signal for notifying the occurrence of the event by vibration. The video signal or the audio signal may be output through the display unit 151 or the sound output module 152 so that the display unit 151 and the sound output module 152 may be classified as a part of the alarm unit 153.

The haptic module 154 generates various tactile effects that the user may feel. A typical example of the tactile effect generated by the haptic module 154 is vibration. The intensity and pattern of the vibration generated by the tactile module 154 is controllable. For example, different vibrations may be combined and output or sequentially output.

In addition to the vibration, the haptic module 154 may generate various tactile effects including effects by stimulus including pin arrangement vertically moving with respect to a contact skin surface, spraying force or suction force of the air through an injection port or a suction port, a touch on the skin surface, contact with an electrode, electrostatic force, and the like and an effect of reproducing a cold and warm sensation using a heat absorbing or heatable element.

The haptic module 154 may be implemented not only to transmit the tactile effect through direct contact but also to allow the user to feel the tactile effect through the muscles of the finger or arm. At least two haptic modules 154 may be provided according to a configuration aspect of the apparatus.

The projector module 155 as a component for performing an image project function by using the apparatus outputting the radiation or the external apparatus receiving the information may display an image which is similar to or at least partially different from an image displayed on the display unit 151 according to a control signal of the controller 180 on an external screen or a wall.

Specifically, the projector module 155 may include a light source (not illustrated) that generates light (for example, laser light) for outputting an image to the outside, an image generating means (not illustrated) for generating an image to be output to the outside using the light generated by the light source, and a lens (not illustrated) for enlarging and outputting the image at a predetermined focal distance to the outside. In addition, the projector module 155 may include a device (not illustrated) capable of adjusting an image projection direction by mechanically moving the lens or the entire module.

The projector module 155 may be divided into a cathode ray tube (CRT) module, a liquid crystal display (LCD) module and a digital light processing (DLP) module according to the type of the display means. In particular, the DLP module may be advantageous for miniaturization of the projector module 151 by enlarging and projecting an image generated by reflecting the light generated from the light source on a digital micromirror device (DMD) chip.

Preferably, the projector module 155 may be provided longitudinally on the side, and a front or back side of the apparatus outputting the radiation or the external apparatus receiving the information. Of course, it is needless to say that the projector module 155 may be provided at any position of the apparatus outputting the radiation or the external apparatus receiving the information as needed.

The memory 160 may store a program for processing and control of the controller 180 and may perform a function for temporarily storing input/output data (e.g., a phone book, a message, an audio, a still image, a moving picture, or the like). The memory 160 may store the frequency (for example, the frequency of use for each telephone number, each message, and each multimedia) of use of each of the data. Further, the memory 160 may store data regarding various patterns of vibrations and sounds output in the touch input on the touch screen.

The memory 160 may include at least one type of storage medium of a flash memory type storage medium, a hard disk type storage medium, a multimedia card micro type storage medium, a card type memory (for example, an SD or XD memory, or the like), a random access memory (RAM), a static random access memory (SRAM), a read-only memory (ROM), an electrically erasable programmable read-only memory (EEPROM), a programmable read-only memory (PROM), a magnetic memory, a magnetic disk, and an optical disk. The apparatus outputting the radiation or the external apparatus receiving the information may operate in connection with a web storage performing a storing function of the memory 160 on the Internet.

The interface unit 170 serves as a passage with all external apparatuses connected to the apparatus outputting the radiation or the external apparatus receiving the information. The interface unit 170 receives data from the external apparatus, transmits the data to each component of the apparatus outputting the radiation or the external apparatus receiving the information receiving the power, or allows data in the apparatus outputting the radiation or the external apparatus receiving the information to be transmitted to the external apparatus. For example, a wireless/wired headset port, an external charger port, a wired/wireless data port, a memory card port, a port connecting a device with an identification module, an audio input/output (I/O) port, a video input/output (I/O) port, an earphone port, and the like may be included in the interface unit 170.

The identification module as a chip for storing various information for authenticating use rights of the apparatus outputting the radiation or the external apparatus receiving the information may include a user identification module (UIM), a subscriber identity module (SIM), a universal subscriber identity module (USIM), and the like. Apparatuses (hereinafter referred to as "identification apparatus") with the identification module may be manufactured in a smart card format. Therefore, the identification apparatus may be connected with the apparatus via the port.

The interface unit may be a passage through which the power from a cradle is supplied to the apparatus when the apparatus is connected to an external cradle or may be a passage through which various command signals input from the cradle by the user are transmitted to the apparatus. The various command signals or the power input from the cradle may serve as a signal for recognizing that the apparatus is correctly mounted on the cradle.

The controller 180 generally controls all motions of the apparatus outputting the radiation or the external apparatus receiving the information.

The controller 180 may include a multimedia module 181 for reproducing multimedia. The multimedia module 181 may be implemented in the controller 180 or implemented apart from the controller 180.

The controller 180 may perform pattern recognition processing to recognize a write input or a drawing input performed on the touch screen as a text or an image.

The power supply unit 190 receives external power and internal power by a control of the controller 180 to supply power required for operations of respective components.

Various embodiments described herein may be implemented in a computer-readable recording medium or a recording medium readable by a device similar to the computer by using, for example, software, hardware, or a combination thereof.

According to hardware implementation, the embodiment described herein may be implemented by using at least one of the application specific integrated circuits (ASICs), the digital signal processors (DSPs), the digital signal processing devices (DSPDs), the programmable logic devices (PLDs), the field programmable gate arrays (FPGAs), the processors, the controllers, the micro-controllers, the microprocessors, and the electric units for performing other functions. In some cases, the embodiments described in the specification may be implemented by the controller 180 itself.

According to software implementation, embodiments such as a procedure and a function described in the specification may be implemented by separate software modules. Each of the software modules may perform one or more functions and operations described in the specification. A software code may be implemented by a software application written by an appropriate program language. The software code may be stored in the memory 160 and executed by the controller 180.

When the configuration of the present invention is applied, there may be provided a system for confirming the movement of a head within a thermoplastic mask by using a pressure sensor and assists controlling the movement of the head, in therapy of head and neck cancer using radiation.

In particular, the pressure sensor is positioned between the mask and the head and a signal of the pressure sensor is represented by a computer programmed system to confirm whether the movement occurs in the mask and support safe radiation therapy of a patient. Further, the radiation therapy may be discontinued when the intensity of the signal is significantly changed due to excessive movement during the therapy.

Detailed description of the preferred embodiments of the present invention disclosed as described above are provided so as for those skilled in the art to implement and execute the present invention. The present invention has been described with reference to the preferred embodiments, but those skilled in the art will understand that the present invention can be variously modified and changed without departing from the scope of the present invention. For example, those skilled in the art may use the respective components disclosed in the embodiments by combining the respective components with each other. Therefore, the present invention is not limited to the embodiments described herein, but intends to grant the widest range which is coherent with the principles and new features disclosed herein.

The present invention may be embodied in other specific forms without departing from the spirit and essential characteristics of the present invention. Accordingly, the aforementioned detailed description should not be construed as restrictive in all terms and should be exemplarily considered. The scope of the present invention should be determined by rational construing of the appended claims and all modifications within an equivalent scope of the present invention are included in the scope of the present invention. The present invention is not limited to the embodiments described herein, but intends to grant the widest range which is coherent with the principles and new features presented herein. Further, the claims that are not expressly cited in the claims are combined to form an embodiment or be included in a new claim by an amendment after the application.

The invention claimed is:

1. A thermoplastic mask apparatus configured for controlled application of radiation therapy to a patient, the thermoplastic mask comprising:
   a thermoplastic mask having a shape determined according to a shape of a first region which is at least a part of the patient's body, wherein the mask is formed for close contact with the first region, the mask being configured to fix the first region of the patient's body to receive radiation from a radiation source; and
   a pressure sensor provided between the mask and the first region to sense both static and dynamic pressures between the mask and the first region, wherein the pressure sensor comprises a deformable diaphragm, frame, beam, or chip portion, and the pressure sensor is configured to indicate a differential pressure when the diaphragm, frame, beam or chip portion is deformed;
   a controller that stops output of radiation from the radiation source if the sensed pressures indicate that the first region is not fixed through the mask.

2. The thermoplastic mask apparatus of claim 1, wherein the pressure sensor further includes a communication unit transmitting information on the sensed pressure to the outside.

3. A system for monitoring a thermoplastic mask
   having a shape determined according to a shape of a first region which is at least a part of a patient's body, wherein the mask is formed for close contact with the first region, the mask being configured to fix the first region of the patient's body to receive radiation from a radiation source;
   a pressure sensor provided between the mask and the first region to sense both static and dynamic pressures between the mask and the first region, wherein the pressure sensor comprises a deformable diaphragm, frame, beam, or chip portion, and the pressure sensor is configured to indicate a differential pressure when the diaphragm, frame, beam, or chip portion is deformed; and
   a communication unit transmitting information on the pressure sensed by the pressure sensor to the outside.

4. The system for monitoring a thermoplastic mask of claim 3, further comprising:
   a controller detecting a change in the sensed pressure to determine whether the first region is fixed through the mask.

5. The system for monitoring a thermoplastic mask of claim 3, further comprising:
   a controller controlling the radiation source to stop an output operation of the radiation when the sensed pressure crosses a predetermined numerical value.

6. The system for monitoring a thermoplastic mask of claim 3, wherein:
   the first region is at least a part of a head of the patient;
   the mask has a shape determined at least according to the part of the head of the patient; and
   wherein the radiation source outputs the radiation in association with a head and neck cancer.

7. The system for monitoring a thermoplastic mask of claim 3, wherein:
   the communication unit adopts at least one of wired communication, short-range communication, and long-range communication;
   the short-range communication includes ANT, Bluetooth, radio frequency identification (RFID), infrared data association (IrDA), and ultra wideband (UWB), Zig-Bee technologies; and the long-range communication includes code division multiple access (CDMA), frequency division multiple access (FDMA), time division multiple access (TDMA), orthogonal frequency division multiple access (OFDMA), and single carrier frequency division multiple access (SC-FDMA).

8. The system for monitoring a thermoplastic mask of claim 3, wherein the pressure sensor includes:
a substrate,
wherein said deformable diaphragm, frame, beam or chip portion is a differential pressure diaphragm installed at the center of the substrate;
a first differential pressure gauge installed on the circumference of the differential pressure diaphragm and formed in a diameter direction to the center of the differential pressure diaphragm;
a second differential pressure gauge interposed at opposed positions between the first differential pressure gauge and the differential pressure diaphragm and formed along a circumferential direction which is orthogonal to the diameter direction on the circumference of the differential pressure diaphragm;
a third differential pressure gauge installed in the vicinity of the first differential pressure gauge on the circumference of the differential pressure diaphragm and installed along the circumferential direction;
a fourth differential pressure gauge interposed at opposed positions between the third differential pressure gauge and the differential pressure diaphragm and formed along the diameter direction on the circumference of the differential pressure diaphragm;
a first static pressure diaphragm installed on an outer portion of the differential pressure diaphragm and interposed between the third differential pressure gauge and the fourth differential pressure gauge in the circumferential direction; and
a second static pressure diaphragm installed on the outer portion of the differential pressure diaphragm and disposed at opposed positions with the differential pressure diaphragm interposed therebetween.

9. The system for monitoring a thermoplastic mask of claim 3, wherein:
the deformable diaphragm, frame, beam, or chip portion is a frame formed of a plurality of beams formed in lattice shape and having a wire groove at an intersection;
the pressure sensor includes:
a strain gauge attached to each of the plurality of beams to measure a strain; and
a frame connected with the end of the lattice shape and covering the plurality of beams;
the beam has a smaller thickness than the frame;
the beam further includes a support supporting the plurality of beams below the intersection of the plurality of beams;
the wire groove is formed to penetrate the intersection and the support;
the sum of the thickness of the intersection and the thickness of the support is equal to the thickness of the frame; and
the support is formed so that an area of a cross-section contacting the intersection is limited within the area of the intersection.

10. The system for monitoring a thermoplastic mask of claim 3, wherein:
the deformable diaphragm, frame, beam, or chip portion comprises a vibratory diaphragm that is incorporated into a silicon die and a capacitor electrode of the pressure sensor;
the silicon die has a silicon die top at an opposite side to a silicon die bottom, a top silicon die port extends from the silicon die top to the top of the vibratory diaphragm through the silicon die, a bottom silicon die port extends from the silicon die bottom to the bottom of the vibratory diaphragm, and the bottom silicon die port has a larger cross-sectional area than the top silicon die port;
the capacitor electrode is positioned to pass through the bottom silicon die port along the bottom of the silicon die; and
the capacitor electrode includes a first signal generating unit positioned throughout the same space as the top silicon die port and a second signal generating unit surrounding the first signal generating unit.

11. A method for administering a thermoplastic mask along with radiation treatment to a patient, comprising:
using the thermoplastic properties of the mask to form the mask according to the shape of a first region which is at least a part of a patient's body;
fixing the mask in close contact with the first region;
outputting radiation from a radiation source to the first region fixed by the mask;
sensing pressure in a space between the mask and the first region by using a pressure sensor provided between the mask and the first region;
transmitting information on the pressure sensed by the pressure sensor to the outside; and
stopping the output of radiation from the radiation source if the sensed pressures indicate that the first region is not fixed through the mask;
wherein to facilitate accurate pressure sensing, the pressure sensor senses both static and dynamic pressures between the mask and the first region, the pressure sensor comprises a deformable diaphragm, frame, beam, or chip portion, and the pressure sensor is configured to indicate a differential pressure when the diaphragm, frame, beam or chip portion is deformed.

12. The method for administering a thermoplastic mask along with radiation treatment to a patient of claim 11, further comprising:
determining whether the first region is fixed through the mask by using a change in the sensed pressure.

13. The method for administering a thermoplastic mask along with radiation treatment to a patient of claim 11, further comprising:
stopping a radiation source from outputting the radiation when the sensed pressure is more than a predetermined numerical value.

14. The method for administering a thermoplastic mask along with radiation treatment to a patient of claim 11, wherein:
the first region is at least a part of a head of the patient; and
the radiation output to the first region is associated with a head and neck cancer.

15. The method for administering a thermoplastic mask along with radiation treatment to a patient of claim 11, wherein:

at least one of wired communication, short-range communication, and long-range communication is used in order to transmit the information to the outside;

the short-range communication includes ANT, Bluetooth, radio frequency identification (RFID), infrared data association (IrDA), and ultra wideband (UWB), ZigBee technologies; and the long-range communication includes code division multiple access (CDMA), frequency division multiple access (FDMA), time division multiple access (TDMA), orthogonal frequency division multiple access (OFDMA), and single carrier frequency division multiple access (SC-FDMA).

* * * * *